(12) United States Patent (10) Patent No.: US 9,186,126 B2
Kusukame et al. (45) Date of Patent: Nov. 17, 2015

(54) ULTRASONIC PROBE AND ULTRASONIC DIAGNOSTIC DEVICE

(75) Inventors: Koichi Kusukame, Nara (JP); Takashi Ogura, Osaka (JP); Takayuki Nagata, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 381 days.

(21) Appl. No.: 13/805,171

(22) PCT Filed: Feb. 13, 2012

(86) PCT No.: PCT/JP2012/000940
§ 371 (c)(1),
(2), (4) Date: Dec. 18, 2012

(87) PCT Pub. No.: WO2012/144117
PCT Pub. Date: Oct. 26, 2012

(65) Prior Publication Data
US 2013/0090561 A1 Apr. 11, 2013

(30) Foreign Application Priority Data

Apr. 21, 2011 (JP) ................................ 2011-095526
Apr. 21, 2011 (JP) ................................ 2011-095527

(51) Int. Cl.
*A61B 8/08* (2006.01)
*A61B 8/00* (2006.01)
(Continued)

(52) U.S. Cl.
CPC ................ *A61B 8/4494* (2013.01); *A61B 8/14* (2013.01); *A61B 8/4444* (2013.01);
(Continued)

(58) Field of Classification Search
CPC ...... A61B 8/4281; A61B 8/14; B06B 1/0622; B06B 1/0292
See application file for complete search history.

(56) References Cited

U.S. PATENT DOCUMENTS 5,974,884 A 11/1999 Sano et al.
7,755,256 B2 7/2010 Shibamoto et al.
(Continued)

FOREIGN PATENT DOCUMENTS

CN 101480345 7/2009
JP 9-65488 3/1997
(Continued)

OTHER PUBLICATIONS

Office Action along with search report issued Jul. 3, 2015 in corresponding Chinese patent application No. 201280001712.4 (with English translation of search report).
(Continued)

*Primary Examiner* — Joel Lamprecht
(74) *Attorney, Agent, or Firm* — Wenderoth, Lind & Ponack, L.L.P.

(57) ABSTRACT

An ultrasonic probe (102) which has high propagation efficiency of ultrasound and can obtain a high resolution ultrasonic diagnostic image. The ultrasonic probe (102) includes an ultrasonic transducer including: a piezoelectric body (208) which generates ultrasound; and a first matching layer (101) which is disposed in a predetermined direction as seen from the piezoelectric body (208) and is for performing acoustic matching between the piezoelectric body (208) and a subject. The first matching layer (101) includes a plurality of matching regions (101a, 101b, 101c) which have a uniform thickness in the predetermined direction, are arranged in a direction perpendicular to the predetermined direction, and include at least two matching regions having frequency characteristics of ultrasound transmittance that are different from each other.

21 Claims, 18 Drawing Sheets

(51) Int. Cl.
  *A61B 8/14*   (2006.01)
  *B06B 1/06*   (2006.01)
  *G10K 11/02*  (2006.01)
  *B82Y 5/00*   (2011.01)

(52) U.S. Cl.
  CPC .............. *A61B 8/4488* (2013.01); *B06B 1/067* (2013.01); *G10K 11/02* (2013.01); *A61B 8/4281* (2013.01); *B82Y 5/00* (2013.01); *Y10S 977/773* (2013.01); *Y10S 977/904* (2013.01)

(56) References Cited

U.S. PATENT DOCUMENTS

2007/0108872 A1   5/2007   Shibamoto et al.
2009/0082673 A1*  3/2009   Lu et al. .................. 600/459

FOREIGN PATENT DOCUMENTS

| | | |
|---|---|---|
| JP | 9-65489      | 3/1997  |
| JP | 11-89835     | 4/1999  |
| JP | 2002-152890  | 5/2002  |
| JP | 2002-305793  | 10/2002 |
| JP | 2003-102095  | 4/2003  |
| JP | 2003-158796  | 5/2003  |
| JP | 2003-299195  | 10/2003 |
| JP | 2003-324797  | 11/2003 |
| JP | 2003-329501  | 11/2003 |
| JP | 2006-288977  | 10/2006 |
| JP | 2006-334074  | 12/2006 |
| JP | 2009-201053  | 9/2009  |

OTHER PUBLICATIONS

International Search Report issued Apr. 10, 2012 in International (PCT) Application No. PCT/JP2012/000940.

* cited by examiner

ULTRASONIC PROBE AND ULTRASONIC DIAGNOSTIC DEVICE

TECHNICAL FIELD

The present invention relates to ultrasonic probes and ultrasonic. diagnostic devices. In particular, the present invention relates to an ultrasonic probe and an ultrasonic diagnostic device that include an ultrasonic transducer, which are used for ultrasonic diagnosis of a subject

BACKGROUND ART

Various imaging technique have been developed in the medical field to observe the inside of a subject to make diagnosis. In particular, ultrasound imaging which obtains internal body information of subject by transmitting and receiving ultrasound allows not only real-time observation of images but also saves the subject from exposure to radiation, unlike other medical image technique such as an X-ray photograph and a radio isotope (RI) scintillation camera etc, Therefore, as highly safe imaging technique, ultrasound imaging is used not only for a fetal diagnosis in obstetrical field but also used for wide range of areas such as the gynecologic system, the circulatory system, and the digestive system. The ultrasound imaging is an image generation technique which takes advantage of the property that the ultrasound is reflected at the boundary of regions having different acoustic impedances (e.g., a boundary of a structure). The contour of a structure that exists inside the subject (e.g., an internal organ, and diseased tissue) is extracted by transmitting the ultrasound beam to the inside of the subject such as a human body, receiving an ultrasound echo generated in the subject, and obtaining a reflecting point at which the ultrasound echo is generated and its reflection intensity.

A device which performs the ultrasound imaging (called, for example, an ultrasonic diagnostic device, and an ultrasonic imaging device) includes a transducer (piezoelectric transducer) as an ultrasonic transducer which transmits and receives ultrasound. The transducer generally used is obtained by forming electrodes on both sides of a piezoelectric body such as a piezoelectric ceramic represented by a Pb (lead) zirconate titanate (PZT), and a polymeric piezoelectric body material represented by a polyvinylidene difluoride (PVDF).

FIG. 2 is a schematic view showing an example of a one-dimensional array type ultrasonic probe. As shown in FIG. 2, an ultrasonic probe 403 that is of a one-dimensional array type includes: a plurality of ultrasonic transducers 205 each including a piezoelectric body 208, a signal electrode 206, a ground electrode 207, and a matching layer 203; a backing 201; a grounding line 202; signal wiring 204; and an acoustic lens 209.

All of the ground electrodes 207 are connected to the one grounding line 202. Each of the signal electrodes 206 is connected to a corresponding one of the signal wiring 204. The signal electrode 206 and the ground electrode 207 are bonded to a pair of opposing surfaces of the piezoelectric body 208. The direction toward the ground electrode 207 as seen from the signal electrode 206 is referred to as +Z. The matching layer 203 is provided on the +Z side with respect to the ground electrode 207.

As shown in FIG. 2, the ultrasonic probe 403 that is of the one-dimensional array type includes a plurality of the ultrasonic transducers 205 arranged in a one-dimensional array on the +Z side of the backing material 201 which absorbs sound waves. Furthermore, further on the +Z side with respect to the ultrasonic transducer 205, the acoustic lens 209 is provided. The ultrasonic probe 403 emits ultrasound to a subject (not shown) via the acoustic lens 209.

The voltage applied to each of the two electrodes 207 and 206 of the ultrasonic transducer 205 causes expansion and contraction of the piezoelectric body 208 due to the piezoelectric effect, and ultrasound is thus generated. It is possible to form an ultrasound beam which is transmitted to a predetermined direction, by arranging the ultrasonic transducers 205 one-dimensionally (or two-dimensionally) as described above, and driving each of the ultrasonic transducers sequentially. Furthermore, the ultrasonic transducer receives the ultrasound reflected off the inside of the body of the subject, and expands or contracts to generate an electric signal. The electric signal is used as a reception signal of the ultrasound.

FIG. 4 is a schematic view showing an example of an ultrasonic diagnostic device. As shown in FIG. 4, an ultrasonic diagnostic device 401 includes an ultrasonic probe 403. The ultrasonic probe 403 and a diagnostic device main body 404 are connected via a cable 405. The diagnostic device main body 404 transmits, via the cable 405, a signal for vibrating the ultrasonic transducer to the ultrasonic probe 403, and creates an image of internal condition of the subject as an ultrasonic diagnostic image based on the signal from the ultrasonic probe 403.

The above-described ultrasonic probe includes the matching layer 203 between the piezoelectric body 208 and the subject due to the following reason.

The propagation efficiency of the ultrasound at the interface where different substances contact each other changes depending on the acoustic impedance of the each of the substances. Specifically, the ultrasound reflects well at the interface where the difference in acoustic impedance is large, which causes large propagation loss of the ultrasound.

In view of this, a matching layer is provided between the ultrasonic transducer and the subject to match the acoustic impedance. The acoustic impedance changes in a stepwise manner through the matching layer from the transducer toward the subject. This lowers reflectance of ultrasound at each of the interfaces and thereby propagation loss of the ultrasound is reduced.

However, providing the matching layer to increase the propagation efficiency of the ultrasound is known to cause an adverse effect, that is, the frequency band becomes narrow and thus the resolution of the ultrasonic diagnostic image becomes degraded. The realization of the matching layer which does not degrade the resolution of the ultrasonic diagnostic image is required.

Conventionally, to build the matching layer which does not degrade the resolution of the ultrasonic diagnostic image, a technique has been disclosed to widen the band by providing, in a plane perpendicular to the propagation direction of the ultrasound, a plurality of regions in which the matching layers have different thicknesses (e.g., patent literature 1).

CITATION LIST

Patent Literature

[PTL 1]
Japanese Unexamined Patent Application Publication No. 2003-299195

SUMMARY OF INVENTION

Technical Problem

As described above, there is a problem that a matching layer, which is provided in an ultrasonic probe to increase the propagation efficiency of the ultrasound, narrows the frequency band of the ultrasound transmitted through the matching layer and causes the degradation of the resolution of the ultrasonic diagnostic image. Thus, an issue is to build the ultrasonic probe which has high propagation efficiency of ultrasound and can obtain a high resolution ultrasonic diagnostic image.

To the above-described issue, the structure described in PTL 1 includes a matching layer including, in a plane perpendicular to the propagation direction of the ultrasound, a plurality of regions having different thicknesses In this case, a time lag is generated among ultrasound pulses transmitted through each of the regions of the matching layer. Providing an acoustic lens does not completely eliminate such time lag, causing a phenomenon in which the ultrasound pulses having time lags are superimposed one another in the body of the subject. This causes the ultrasound emitted from the matching layer to have a waveform different from the ideal impulse waveform, which causes degradation in resolution in the propagation direction of the ultrasound in the ultrasonic diagnostic image. Therefore, the technique disclosed by PTL 1 does not solve the above-described issue.

The present invention is conceived to solve the aforementioned conventional issues and has an object to provide the ultrasonic probe and the like which have high propagation efficiency of the ultrasound and can obtain a high resolution ultrasonic diagnostic image.

Solution to Problem

In order to achieve the aforementioned object, an ultrasonic probe according to an aspect of the present invention is an ultrasonic probe used for ultrasonic diagnosis of a subject, the ultrasonic probe includes an ultrasonic transducer including: a piezoelectric body which generates ultrasound; and a first matching layer which is disposed in a predetermined direction as seen from the piezoelectric body and is for performing acoustic matching between the piezoelectric body and the subject, wherein the first matching layer includes a plurality of matching regions which have a uniform thickness in the predetermined direction, are arranged in a direction perpendicular to the predetermined direction, and include at least two matching regions having frequency characteristics of ultrasound transmittance different from each other.

With this, it is possible to widen frequency band of ultrasound which passes through the matching layer compared to the conventional matching layer having a uniform frequency characteristic. The reason for this is that frequency characteristic of ultrasound which passes through each of the matching regions is different, and thus the ultrasound which passed through each of the matching regions added to the entire matching layer is wider in frequency band than the ultrasound which passed through the conventional matching layer having the uniform frequency characteristic. In addition, the thickness of the matching region in the ultrasound propagation direction (the predetermined direction) is constant, and thus time lag does not occur to the ultrasound pulse which passes through the respective matching regions. As a result, the ultrasound pulse is propagated to the subject with a waveform close to the impulse waveform. This makes it possible to obtain a high-resolution ultrasonic diagnostic image.

Furthermore, it is preferable that the matching regions include at least two matching regions having densities different from each other.

With this, it is possible to realize the matching regions having different frequency characteristics of ultrasound transmittance. The reason for this is that the matching regions having different densities have different frequency characteristics of ultrasound transmittance.

Furthermore, it is preferable that the first matching layer include a plurality of matching materials which have different acoustic impedances, and at least one of the matching materials have tapered shapes parallel to the predetermined direction, and each of the tapered shapes have a thickness which continuously increases or decreases in the predetermined direction.

With this, it is possible to allow part of the matching layer closer to the piezoelectric body to have an acoustic impedance close to an acoustic impedance of the piezoelectric body, and allow part of the matching layer closer to the subject to have an acoustic impedance close to an acoustic impedance of the subject. Furthermore, it is possible to allow the acoustic impedance in the matching layer to continuously change in the propagation direction of the ultrasound.

Furthermore, it is preferable that the number of the tapered shapes in a unit area in one of the matching regions be different from the number of the tapered shapes in a unit area in an other one of the matching regions, the unit areas each being in a plane perpendicular to the predetermined direction.

With this, it is possible to realize the matching regions having different frequency characteristics of ultrasound transmittance. The reason for this is that the matching regions in which the densities of the tapered shapes are different have different frequency characteristics of ultrasound transmittance.

Furthermore, it is preferable that a size of the at least one of the matching materials which has the tapered shapes in one of the matching regions be different from a size of the tapered shapes in an other one of the matching regions, the sizes each being in the predetermined direction.

With this, it is possible to realize the matching regions having different frequency characteristics of ultrasound transmittance. The reason for this is that the matching regions in which the heights, in the ultrasound propagation direction, of the tapered shapes are different have different frequency characteristics of ultrasound transmittance.

Furthermore, it is preferable that a width of the at least one of the matching materials which has the tapered shapes in one of the matching regions be different from a width of the at least one of the matching materials which has the tapered shapes in an other one of the matching regions, the widths each being in a direction in which the matching regions are arranged.

With this, it is possible to realize the matching regions having different frequency characteristics of ultrasound transmittance. The reason for this is that the matching, regions in which the thicknesses of the tapered shapes are different have a different frequency characteristic of ultrasound transmittance.

Furthermore, it is preferable that, out of a front surface and a back surface of the first matching layer, a surface which is more distant from the piezoelectric body be flat.

With this, the contact surface between the matching layer and an acoustic lens is flat, and the ultrasonic probe can receive, in a wide range of temperature, ultrasound in a wide band. As a result, a high-resolution ultrasonic diagnostic image can be obtained. The reason for this is that the acoustic lens has a high rate of shrinkage with respect to a change in temperature. Thus, the acoustic lens may be detached due to shrinkage of the acoustic lens if the contact surface is not flat.

Furthermore, it is preferable that the first matching layer include a plurality of matching sub-layers stacked in the predetermined direction, and at least one of the matching sub-layers include a plurality of matching regions which (i)

are arranged in a direction perpendicular to the predetermined direction, and (ii) have different frequency characteristics of ultrasound transmittance.

With this, the acoustic matching between the piezoelectric body and the subject can be performed with higher precision and, at the same time, it is possible to widen the frequency band of the ultrasound which passes through the matching layer. The reason for this is that the matching sub-layers having different acoustic impedances make it possible to perform acoustic matching in a stepwise manner from the piezoelectric body to the subject, and the matching regions makes it possible to increase the frequency characteristics of ultrasound transmittance.

Furthermore, it is preferable that each of the matching sub-layers have a uniform thickness in the predetermined direction.

With this, the ultrasonic probe can receive, in a wide range of temperature, ultrasound in a wide band. As a result, a high-resolution ultrasonic diagnostic image can be obtained. The reason for this is that the matching sub-layers may be detached from each other due to the difference in rate of shrinkage of the matching sub-layers with respect to the change in temperature if each of the matching sub-layers does not have a constant thickness.

Furthermore, it is preferable that the first matching layer be formed from a mixture obtained by mixing a plurality of materials in a predetermined mixing ratio, and a mixing ratio in one of the matching regions is different from a mixing ratio in an other one of the matching regions.

Furthermore, it is preferable that the first matching layer include a sintered material.

Furthermore, it is preferable that the first matching layer include at least silicon dioxide and at least one material out of silver, copper, and an acrylic material.

Furthermore, it is preferable that the first matching layer include, as material, a plurality of particles which are different in diameter by at least five times.

With this, it is possible to realize the matching regions having different frequency characteristics of ultrasound transmittance. The reason for this is that each of the matching regions in which materials of the mixtures are mixed in different mixing ratio has a different frequency characteristic of ultrasound transmittance.

Furthermore, it is preferable that a width of each of the matching regions in a direction in which the matching regions are arranged be greater than or equal to a wavelength of ultrasound used for the ultrasonic diagnosis.

With this, it is possible to build the matching regions having different frequency characteristics of ultrasound transmittance, The reason for this is that, when the width of the matching region is smaller than the wavelength of the ultrasound, the matching region of which frequency characteristic of ultrasound transmittance is a predetermined value is not formed.

Furthermore, it is preferable that the first matching layer include metal nano particles each of which has a diameter less than or equal to one micron, and at least part of the first matching layer be metal bulked, the first matching layer having density determined by a mixing ratio of the metal nano particles to the first matching layer.

With this, it is possible to efficiently manufacture the matching materials having different densities. The reason for this is that the matching materials having different densities can be manufacture by using the same materials and changing their mixing ratios, Furthermore, it is preferable that the ultrasonic transducer further include: a backing material which is disposed on a side opposite to a side on which the first matching layer is disposed with respect to the piezoelectric body and absorbs ultrasound; and a second matching layer disposed between the backing material and the piezoelectric body, and including a plurality of matching regions which are arranged in a direction perpendicular to the predetermined direction and each of which allows ultrasound of different frequency to be transmitted.

With this, it is possible to increase the sound pressure of the ultrasound that is propagated toward the direction of the subject from the piezoelectric body.

Furthermore, it is preferable that the ultrasonic transducer further include: a backing material which is disposed on a side opposite to a side on which the first matching layer is disposed with respect to the piezoelectric body and absorbs ultrasound; and a high reflective layer disposed between the backing material and the piezoelectric body, and having a property of reflecting ultrasound.

With this, it is possible to widen the frequency band of the ultrasound which passes through the matching layer.

Furthermore, it is preferable that the ultrasonic transducers be arranged in a one-dimensional array, and in each of the ultrasonic transducers, an average frequency that is an average value of frequency of ultrasound transmitted through the matching regions located at each of ends of the ultrasonic transducer in a direction in which the matching regions are arranged is lower than an average frequency that is an average value of frequency of ultrasound transmitted through one or more of the matching regions located in the center of the ultrasonic transducer in the direction in which the matching regions are arranged.

With this, it is possible to obtain a high-resolution ultrasonic diagnostic. image.

Furthermore, it is preferable that the ultrasonic transducers be arranged in a one-dimensional array, and in each of the ultrasonic transducers, an average frequency that is an average value of frequency of ultrasound transmitted through the matching regions located at each of ends of the ultrasonic transducer in a direction in which the matching regions are arranged is higher than an average frequency that is an average value of frequency of ultrasound transmitted through one or more of the matching regions located in the center of the ultrasonic transducer in the direction in which the matching regions are arranged.

With this, it is possible to obtain the ultrasonic diagnostic image with a high signal to noise ratio (S/N).

Furthermore, it is preferable that the ultrasonic transducers be arranged in a one-dimensional array, and the matching regions in one of the ultrasonic transducers be arranged in an order different from an order of the matching regions in an other one of the ultrasonic transducers.

Furthermore, it is preferable that the ultrasonic transducers be arranged in a one-dimensional array, and the matching regions in each of the ultrasonic transducers be arranged in an order to form a cyclic pattern in the ultrasonic probe.

With these, it is possible to obtain an ultrasonic diagnostic image in high resolution with high S/N.

Furthermore, an ultrasonic diagnostic device according to an aspect of the present invention includes: an ultrasonic probe; and a diagnostic device which generates a signal for causing the piezoelectric body to generate ultrasound, and generates an ultrasonic diagnostic image based on a signal received by the ultrasonic probe from the subject.

With this, it is possible to produce the effects of the above-described ultrasonic probe to perform ultrasonic diagnosis on the subject.

Advantageous Effects of Invention

With an ultrasonic probe or the like according to the present invention, a matching layer which does not cause degradation of resolution of the ultrasonic diagnostic image is built, and thus it is possible to obtain a high resolution diagnostic image for ultrasonic diagnosis.

DESCRIPTION OF EMBODIMENTS

Hereinafter, embodiments of the present invention shall be described with reference to the Drawings. It should be noted that each of the embodiments described hereafter illustrates a preferred specific example of the present invention. Numerical values, shapes, materials, constituent elements, the positioning and connection configuration of the constituent elements, steps, the sequence of the steps, and so on, described in the embodiments below are merely examples and are not intended to limit the present invention. Furthermore, among the constituent elements in the following embodiments, those constituent elements which are not described in the independent claims indicating the broadest concept of the present invention are described as optional constituent elements for configuring a more preferable embodiment.

Furthermore, the same constituent elements are assigned with the same reference signs, and detailed descriptions thereof may be omitted.

(Embodiment 1)

Figure 1:
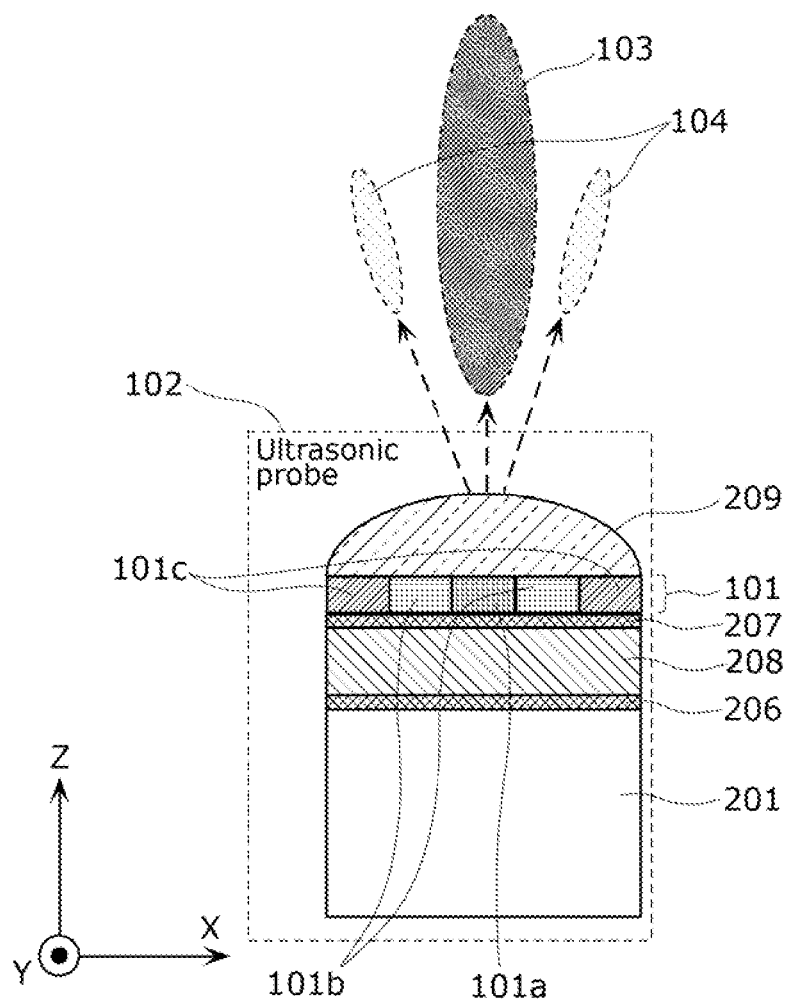
FIG. 1 is a cross-sectional view of an example of an ultrasonic probe according to Embodiment 1 of the present invention.

FIG. 1 is a cross-sectional view of an example of an ultrasonic probe according to Embodiment 1 of the present invention.

As shown in FIG. 1, an ultrasonic probe 102 according to this embodiment includes a piezoelectric body 208, a signal electrode 206, and a ground electrode 207. Furthermore, it is more preferable that the ultrasonic probe 102 further include a backing 201, and the acoustic lens 209.

The ultrasonic probe 102 is different from a conventional ultrasonic probe 304 in that the ultrasonic probe 102 includes a matching layer 101 between the ground electrode 207 and a subject (not shown).

The matching layer 101 includes a plurality of matching regions arranged in the X-direction and each having a different transmittance of ultrasound. The matching layer 101 is designed so that a matching region 101a located in the center in the X-direction transmits, at the highest rate, the ultrasound generated by the piezoelectric body 208, and that the transmittance decreases towards both ends which are a matching region 101b and a matching region 101c. Therefore, the ultrasound which passes through the matching region 101a located in the center has the highest sound pressure, and the ultrasound which passes through each of the matching regions 101c located at each of the ends has the lowest sound pressure. The ultrasonic diagnosis with high S/N can be realized by using, with the ultrasonic diagnostic device (FIG. 4), the ultrasonic probe according to the present invention instead of the conventional ultrasonic probe.

Figure 3:
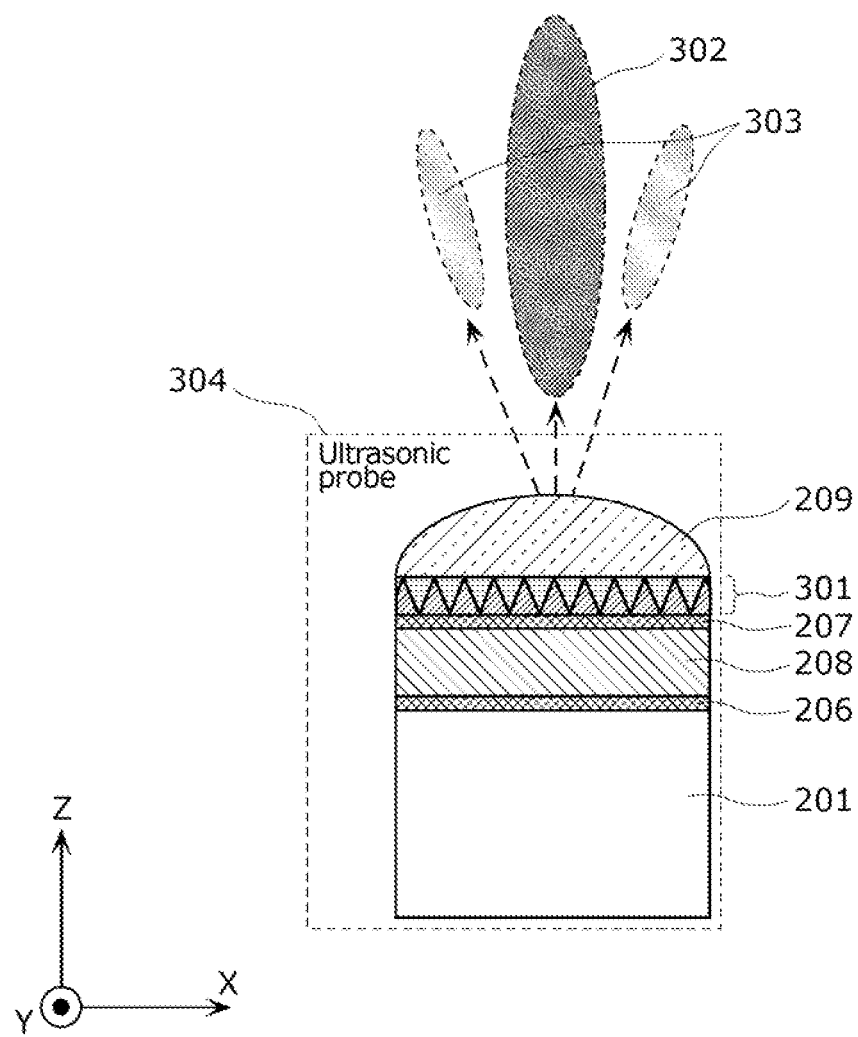
FIG. 3 is a cross-sectional view of a conventional ultrasonic probe.

The following describes the reason why the ultrasonic diagnosis with a high S/N can be performed using the ultrasonic probe according to the present invention FIG. 3 is a cross-sectional view of the conventional ultrasonic probe. When frequency characteristic of a sound pressure of ultrasound emitted from a surface of the ultrasonic probe is constant on the surface, a side lobe 303 is formed in the body of a subject in addition to a main lobe 302. The ultrasonic diagnostic image includes the image obtained by the main lobe 302 on which the image obtained by the side lobe 303 is superimposed as a noise. The generation of the side lobe causes degradation of S/N (signal to noise ratio) of the ultrasonic diagnostic image.

With the ultrasonic probe 102 shown in FIG. 1, the sound pressure of the ultrasound which passes through the matching region 101a located in the center is increased to be higher than the sound pressure of the ultrasound which passes through the matching regions located at each of the ends. This makes it possible to lower the sound pressure of side lobe 104 than the sound pressure of the conventional ultrasonic probe. Due to the above, the ultrasonic diagnosis with high S/N can be realized.

Here, an example of a method for building a matching layer including a plurality of regions having different transmittance (hereinafter also referred to as a multi-transmittance layer) is described.

Figure 7:
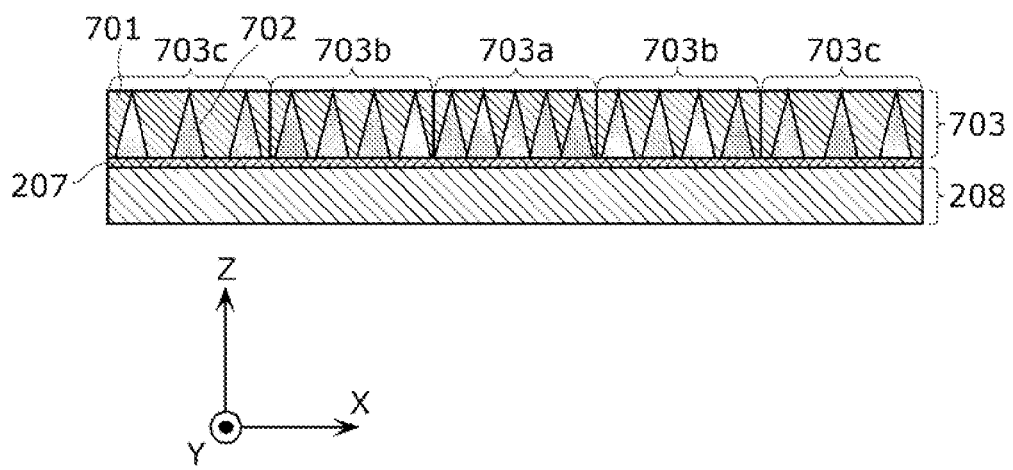
FIG. 7 is a cross-sectional view of an example of a multi-transmittance layer of the ultrasonic probe according to Embodiment 1 of the present invention.

FIG. 7 is a cross-sectional view of an example of a multi-transmittance layer of the ultrasonic probe according to this embodiment.

A matching layer 703 shown in FIG. 7 includes: a first matching material 702 having an acoustic impedance close to an acoustic impedance of the piezoelectric body 208; and a second matching material 701 having an acoustic impedance close to an acoustic impedance of living body tissue of the subject. The first matching material 702 is conical in shape. A plurality of the first matching materials 702 are provided with their bases located on the side of the piezoelectric body 208 and their vertexes located on the side of the subject. Furthermore, the portion of the matching layer 703 other than the portion filled by the first matching material 702 is filled by the second matching material 701.

Here, the first matching material 702 which is conical in shape is made from a composite material obtained by mixing a metal, a semiconductor, ceramics, or resin with metal or oxide. The range of the acoustic impedance of the first matching material 702 is from 10 to 30 MRayl. The second matching material 701 is made from a composite material obtained by mixing various resins or mixing resin with metal or oxide. The range of the acoustic impedance of the second matching material 701 is from 1.2 to 3 MRayl. In general, the range of the acoustic impedance of the piezoelectric body 208 is from 20 to 30 MRayl, and the acoustic impedance of the living body tissue of the subject is approximately 1.5 MRayl. Therefore, arranging the first matching material and the second matching material as described above makes it possible to reduce the difference in acoustic impedance between both the matching layer and the piezoelectric body, and between the matching layer and the living body tissue of the subject.

The following describes specific examples of the above material. Examples of the first matching material 702 include: aluminum (17 MRayl), lead (22 MRayl), silicon (20 MRayl), a mixture of approximately 95% silver and approximately 5% silicon dioxide (16 MRayl), and crystal (16 MRayl). Examples of the second matching material 701 include: plastics, rubber and the like, such as silicone rubber (1.5 MRayl), acrylic resin (3 MRayl), and polyimide (3 MRayl).

The matching layer 703 includes matching regions 703a, 703b, and 703c each of which includes the cones made from the first matching material 702. The cones are arranged at different intervals depending on the region. Specifically, the intervals between the cones are smallest in the matching region 703a located in the center in the X-direction, and the intervals between the cones increases toward each of the ends, that is, the intervals between the cones are greater in the matching regions 703b and 703c.

In this manner, the region in which cones are arranged at greater intervals transmits the ultrasound at a lower rate. Thus, it is possible to design a multi-transmittance layer having an arbitrary transmittance can be designed by adjusting the intervals between the cones for each of the regions.

Furthermore, it is preferable that the intervals between the cones be less than or equal to a quarter of a wavelength of the ultrasound in the region having the biggest intervals, With this, it is possible to build an ultrasonic probe which has high sensitivity and allows observation of a deeper portion.

Figure 8:
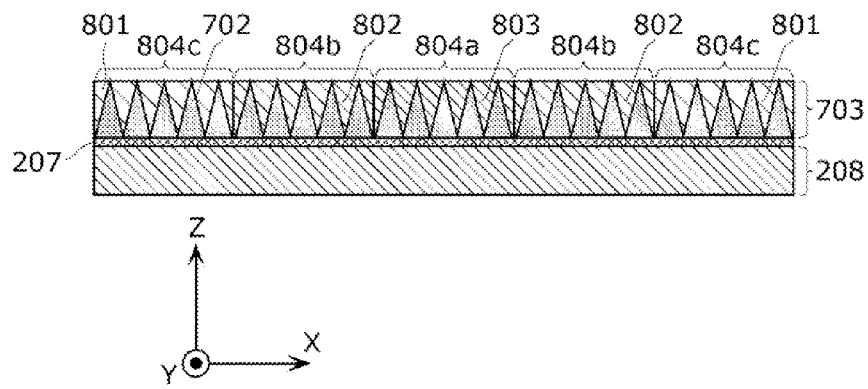
FIG. 8 is a cross-sectional view of another example of the multi-transmittance layer of the ultrasonic probe according to Embodiment 1 of the present invention.

FIG. 8 is a cross-sectional view of another example of a multi-transmittance layer of the ultrasonic probe according to this embodiment.

A matching layer 804 shown in FIG. 8 includes: a first matching material 702 having an acoustic impedance close to an acoustic impedance of the piezoelectric body 208; and a second matching material having an acoustic impedance close to an acoustic impedance of living body tissue of the subject. The first matching material 702 is conical in shape. A plurality of the first matching materials 702 are provided with their bases located on the side of the piezoelectric body 208 and their vertexes located on the side of the subject. Furthermore, the portion of the matching layer 804 other than the portion filled by the first matching material 702 is filled by the second matching materials 803, 802, and 801.

In the matching layer 804, matching regions 804a, 804b, and 804c includes second matching materials 803, 802, and,

801, respectively. The second matching materials are selected so that the acoustic impedance of the second matching material 803 has an acoustic impedance closest to the acoustic impedance of the piezoelectric body 208, and the regions closer to each of the ends includes materials, which are the second matching materials 802 and 801, having greater difference in acoustic impedance with respect to the piezoelectric body 208.

In this manner, the closer the acoustic impedance of the second matching material is to the acoustic impedance of the piezoelectric body, the higher the transmittance is, Thus, it is possible to design a multi-transmittance layer by adjusting the acoustic impedance of the second matching material for each of the regions.

It should be noted that, in an example described here, the multi-transmittance layer in which the acoustic impedances of the second matching materials are different depending on the matching regions. However, the multi-transmittance layer in which the acoustic impedance of the second matching materials is uniform and the acoustic impedances of the first matching materials are different depending on the matching regions is also acceptable. In this case, the closer the acoustic impedance of the first matching material is to the acoustic impedance of the subject, the higher the transmittance is, Thus, it is possible to design a multi-transmittance layer by adjusting the acoustic impedance of the first matching material. With this, it is possible to enhance S/N in the ultrasonic diagnosis.

It should be noted that the structure in which the first matching materials and the second matching materials are different depending on the regions is also acceptable.

However, a material which is hard to process, such as a metal, is often used as a second matching material. Thus, it is preferable that the second matching material be of one type. Use of the second matching material of one type makes it possible to provide the ultrasonic probe more inexpensively.

It should be noted that many materials of the first matching materials have significantly different coefficients of thermal expansion depending on the materials, and thus it is preferable that the first matching material of one type be used. This makes it possible to provide the ultrasonic probe more superior in heat resistance.

As described above, the ultrasonic probe 102 of the present invention can be built, by using the matching layer 703 and the matching layer 804 that are the multi-transmittance layers as the matching layer 101 in FIG. 1.

It should be noted that the matching layer 703 can be manufactured at a lower cost than the matching layer 804. The matching layer 804 has less wavelength dependency compared to the matching layer 703, and is easy to design. Thus, it is preferable that an optimal structure be used depending on the applications.

It should be noted that the multi-transmittance layer in which both the matching materials and the intervals of the cones are different for each of the regions makes it possible to design the transmittance of matching layer more freely with a small number of types of matching material, and thus is preferable.

Figure 9:
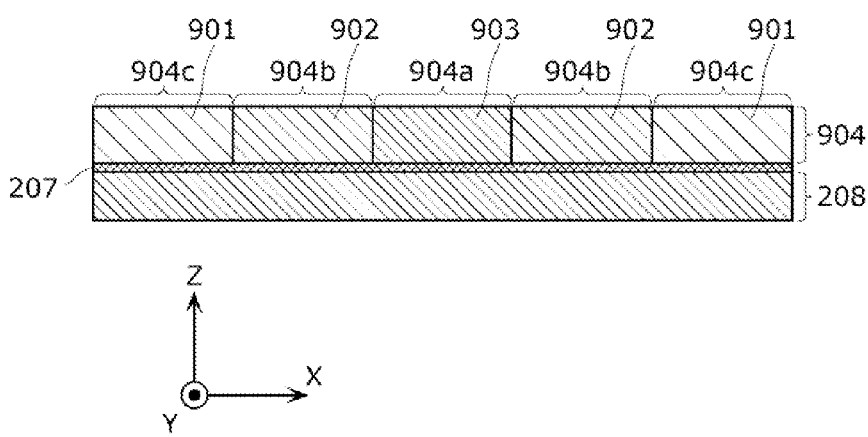
FIG. 9 is a cross-sectional view of another example of the multi-transmittance layer of the ultrasonic probe according to Embodiment 1 of the present invention.

FIG. 9 is a cross-sectional view of another example of the multi-transmittance layer of the ultrasonic probe according to this embodiment.

In the matching layer 904 shown in FIG. 9, each of the matching regions 904a, 904b, and 904c is made from one type of matching materials 903, 902, and 901, respectively, Furthermore, the matching materials 901, 902, and 903 are made from materials having acoustic impedances different from one another. In this manner, even when each of the matching regions is made from one type of the matching material (i.e., conic structures shown in FIG. 7 and. FIG. 8 are absent), the transmittance is different in each of the regions, when each of the matching regions includes a material having a different acoustic impedance. Thus, it is apparent that characteristics of the matching layer of the present invention are satisfied. With this, it is possible to enhance S/N in the ultrasonic diagnosis.

Hereinafter, the matching layer including a plurality of matching regions having different acoustic impedances as described above is referred to as a multi-impedance layer.

Furthermore, it is preferable that the speed of sound be approximately uniform in each matching region, and each matching region have an almost uniform thickness. With this, a time lag in the ultrasound which passed through the respective regions is reduced, and thus the resolution in the propagation direction of the ultrasound increases.

In this manner, when the sound field inside the body of the subject is designed with the structure shown in FIG. 9 (multi-impedance layer), use of a mixture material made from a plurality of materials having different acoustic impedances is more preferable in order to allow designing of arbitrary transmittance.

The inventors of the present invention conducted dedicated studies to prepare a plurality of materials having different acoustic impedances, and found such materials can be obtained as follows.

Figure 10:
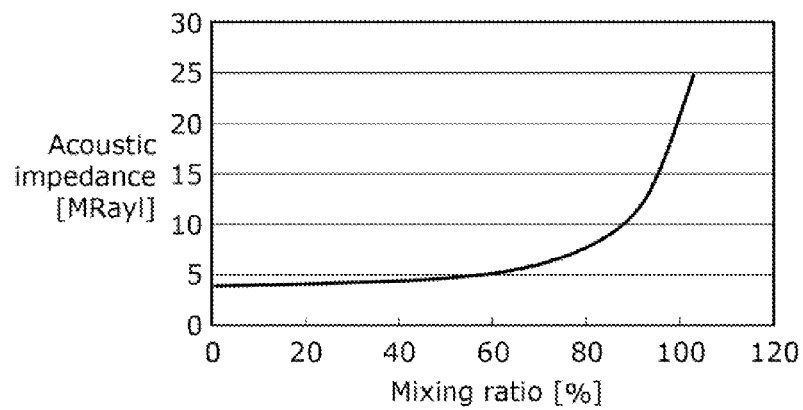
FIG. 10 is a diagram showing a relationship between an acoustic impedance and a mixing ratio of silver to a mixture which includes the silver.

FIG. 10 is a diagram showing a relationship between an acoustic impedance and a mixing ratio of silver to a mixture which includes silver and silicon dioxide. The unique study conducted by the inventors of the present invention revealed that it is possible to obtain a material having an arbitrary acoustic impedance at least in a range from 3.8 to 25 MRayl, by adjusting a mixing ratio of silver to a mixture, which includes silver and silicon dioxide, as shown in FIG. 10.

Figure 11:
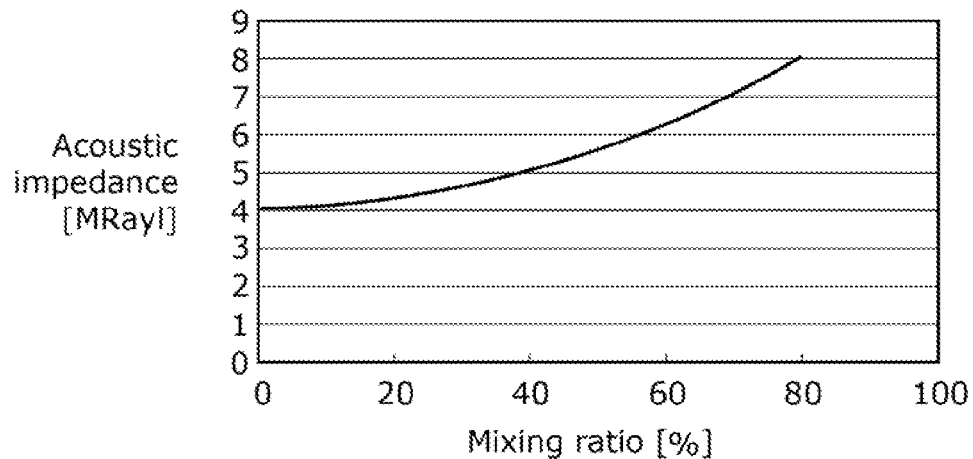
FIG. 11 is a diagram showing the relationship between an acoustic impedance and a mixing ratio of copper to a mixture which includes the copper.

FIG. 11 is a diagram showing a relationship between an acoustic impedance and a mixing ratio of copper to a mixture which includes copper and silicon dioxide. The unique study conducted by the inventors of the present invention revealed that it is possible to obtain a material having an arbitrary acoustic impedance at least in a range from 4 to 8 MRayl, by changing a mixing ratio of copper to a mixture, which includes silver and silicon dioxide, as shown in FIG. 11.

Figure 12:
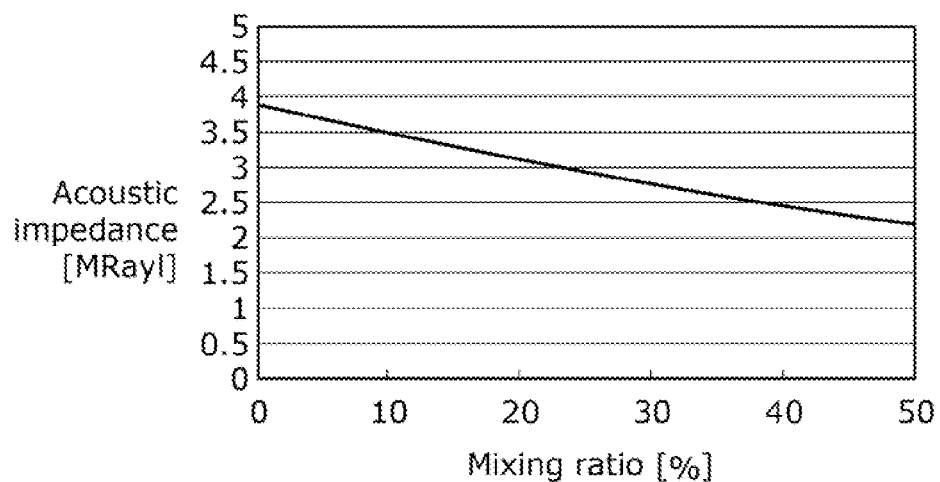
FIG. 12 is a diagram showing a relationship between an acoustic impedance and a mixing ratio of acryl to a mixture which includes the acryl.

FIG. 12 is a diagram showing a relationship between an acoustic impedance and a mixing ratio of acryl to a mixture which includes acryl and silicon dioxide. The unique study conducted by the inventors of the present invention revealed that it is possible to obtain a material having an arbitrary acoustic impedance at least in a range from 2.2 to 3.8 MRayl, by changing a mixing ratio of copper to a mixture, which includes acryl and silicon dioxide, as shown in FIG. 12.

In this manner, it is possible to manufacture a material having an arbitrary acoustic impedance by using a mixture material which includes a plurality of materials. Thus, it is possible to design arbitrary transmittance.

Thus, transmittance can be designed freely, which produces a greater effect in reducing the side lobe, and enhances S/N in ultrasonic diagnosis.

The above described the examples, with reference to FIGS. 7 to 9, the matching layers each of which includes three types of matching regions, and has the sound pressure that gradually decreases toward each of the ends of the matching layer. However, it is preferable that the ultrasonic probe of the present invention include a greater number of matching regions in the matching layer. Specifically, as shown by a solid line 501 in FIG. 5, the structure which allows the sound pressure to continuously decrease from the center toward the each of the ends is more preferable.

Furthermore, the sound pressure distribution close to Gaussian distribution of which center is in the matching region located in the center is even more preferable. With this, the side lobe can be further reduced.

In the case of the ultrasonic diagnostic device which can perform a three-dimensional ultrasonic diagnosis by scanning the ultrasound in the X-direction, it is possible to achieve an effect of increased resolution in the X-direction (scan direction).

Furthermore, the structures of the matching layer shown in FIG. 7 and FIG. 8 make it possible to widen the band compared to the band of the matching layer which includes a multi-impedance layer (FIG. 9), and thus is more preferable in this regard. Furthermore, the matching layer shown in FIG. 9 can be manufactured at a lower cost than the matching layers shown in FIG. 7 and FIG. 8, and thus is more preferable in this regard.

Furthermore, it is preferable that (position) distribution of the sound pressure of the ultrasound on the surface of the ultrasonic probe be different for each frequency. As shown by an example in FIG. 5, it is preferable that the higher the frequency is, the narrower the width in the X-direction be having localized sound pressure distribution as shown by a dotted line 502; and the lower the frequency is, the broader the width in the X-direction be having gentle sound pressure distribution as shown by a solid line 501.

This makes it possible to reduce variation in energy ratio between the main lobe 103 and the side lobe 104 of the ultrasound having a high frequency and the ultrasound having a low frequency, and thus an ultrasound pulse waveform inside the subject becomes more stable. Thus, the resolution in the propagation direction (Z direction) of the ultrasound increases in the ultrasonic diagnostic image of the inside of the subject.

Figure 5:
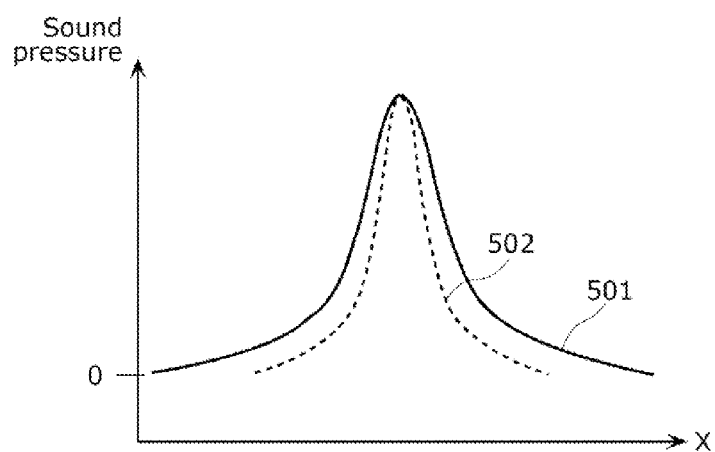
FIG. 5 is a diagram showing sound pressure distribution at the contact surface between a subject and the ultrasonic probe according to Embodiment 1.

Furthermore, for example, in FIG. 5, when it is defined that a width in the X-direction at which the sound pressure is the half of the sound pressure in the center of the matching region is a half-width, it is more preferable that the half-width be in inverse proportion to frequency. With this, it is possible to further increase the SIN in the ultrasonic diagnosis.

In this manner, to allow the contact surface between the ultrasonic probe and the subject to have a different sound pressure distribution for each frequency, it is necessary to realize the matching layer which includes a plurality of regions which are different in transmittance frequency characteristics (i.e. shape of a graph in which the vertical axis indicates transmittance and the horizontal axis indicates frequency is different). The following describes such embodiment.

Figure 13:
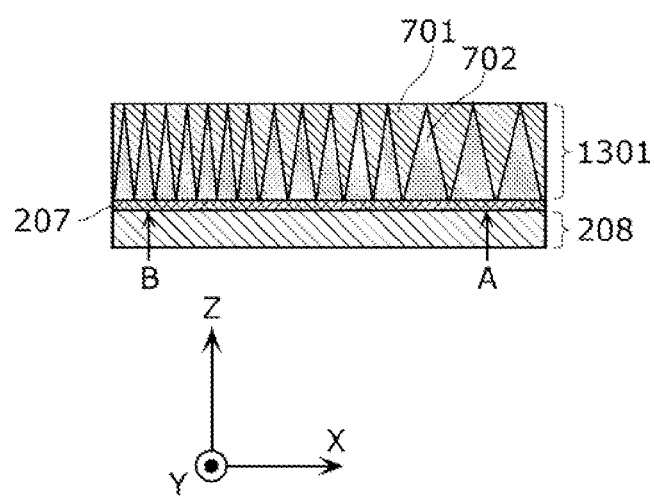
FIG. 13 is a cross-sectional view of an example of a matching layer of the ultrasonic probe according to Embodiment 1 of the present invention.

FIG. 13 is a cross-sectional view of an example of the matching layer of the ultrasonic probe according to Embodiment 1 of the present invention. The following describes a matching layer 1301 shown in FIG. 13. The matching layer 1301 is an example of a matching layer including a plurality of regions which have different frequency characteristics of transmittance (hereinafter referred to as a multi-transmittance F characteristic layer).

As with the matching layer 703, the matching layer 1301 includes: the first matching material 702 having an acoustic impedance close to an acoustic impedance of the piezoelectric body 208; and the second matching material 701 having an acoustic impedance close to an acoustic impedance of living body tissue of the subject. A plurality of the first matching materials 702 each of which is conical in shape are provided with their bases positioned on the side of the piezoelectric body 208 and their vertexes positioned on the side of the subject. Furthermore, the portion of the matching layer 1301 other than the portion filled by the first matching material 702 is filled by the second matching material 701. Furthermore, in the matching layer 1301, the base area of the cones made from the first matching material 702, and the intervals between the adjacent cones are largest in the vicinity of point A in FIG. 13, and the base area of cone decreases toward the point B and, along with this, the intervals between the adjacent cones become smaller.

In this manner, in the matching layer in which the intervals between the cones are different depending on the portion, it is possible to allow the value defined by (transmittance of low frequency)/(transmittance of high frequency) to be larger in a portion in which the intervals between the cones are larger. Thus, the multi-transmittance F characteristic layer can be realized.

Figure 14:
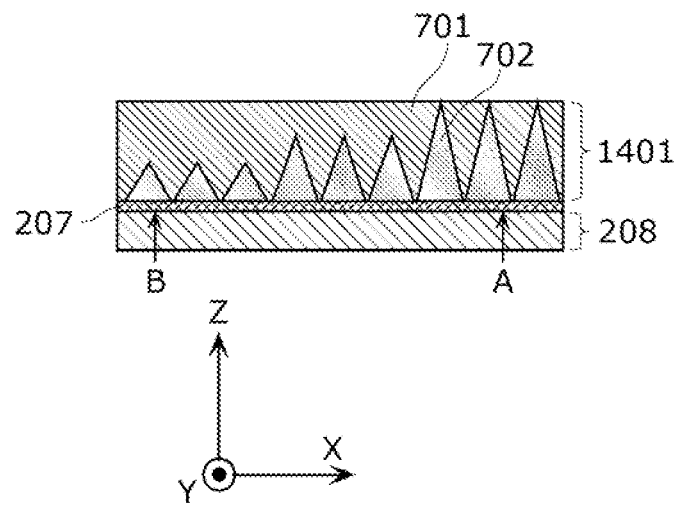
FIG. 14 is a cross-sectional view of another example of the matching layer of the ultrasonic probe according to Embodiment 1 of the present invention.

FIG. 14 is a cross-sectional view of another example of the matching layer of the ultrasonic probe according to this embodiment. The following describes a matching layer 1401 shown in FIG. 14, which is another example of the multi-transmittance F characteristic layer.

As with the matching layer 703, the matching layer 1401 includes: the first matching material 702 having an acoustic impedance close to the acoustic impedance of the piezoelectric body 208; and the second matching material 701 having an acoustic impedance close to an acoustic impedance of living body tissue of the subject. The first matching materials 702 each of which is conical in shape are arranged with their bases positioned on the side of the piezoelectric body 208 and their vertexes positioned on the side of the subject. Furthermore, the portion of the matching layer 1401 other than the portion filled by the first matching material 702 is filled by the second matching material 701. Furthermore, in the matching layer 1401, the height of the cone made from the first matching material 702 is highest in the vicinity of point A in FIG. 14, and the height of the cone decreases toward the point B. In this manner, in the matching layer in which the heights of cones are different depending on the portion, it is possible to allow the value defined by (transmittance of low frequency)/(transmittance of high frequency) to be larger when the height of the cone is higher. Thus, the multi-transmittance F characteristic layer can be realized.

The inventors of the present invention conducted dedicated studies to realize the multi-transmittance F characteristic layer, and found such layer can be obtained as follows.

Figure 16:
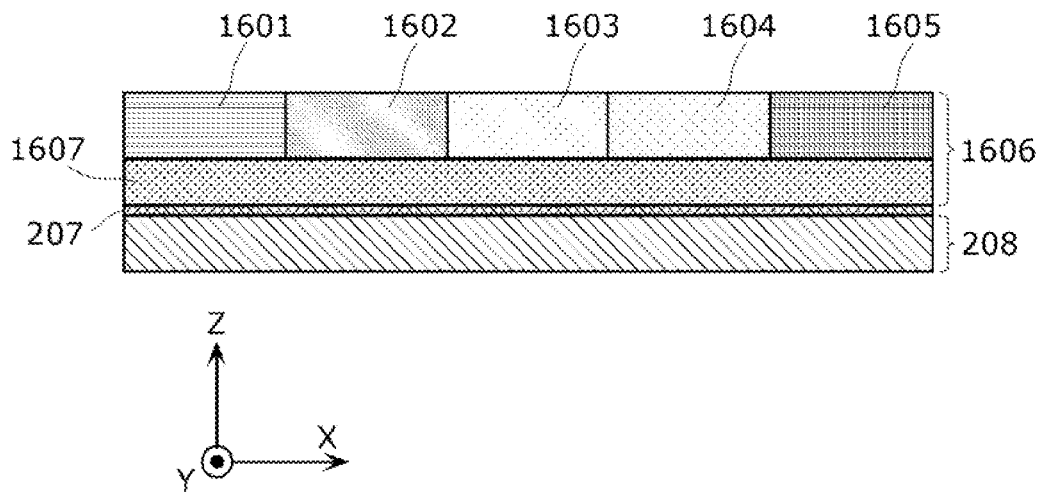
FIG. 16 is a cross-sectional view of another example of the matching layer of the ultrasonic probe according to Embodiment 1 of the present invention.

FIG. 16 is a cross-sectional view of another example of the matching layer of the ultrasonic probe according to this embodiment. The following describes a matching layer 1606 shown in FIG. 16, which is another example of the multi-transmittance F characteristic layer.

The matching layer 1606 is a matching layer in which two layers are stacked. The two layers are: a matching layer 1607 on the side of the piezoelectric body made from a mixture of approximately 90% silver and approximately 10% silicon dioxide (approximately 11.9 MRayl; thickness: approximately 45 μm); and a multi-impedance layer on the side of the subject and including five types of matching materials 1601, 1602, 1603, 1604, and 1605. It should be noted that each of the layers included in the matching layer, which includes the layers as described above, is also referred to as a matching sub-layer.

Furthermore, the matching material 1601 is made from a mixture of approximately 85% silver, and approximately 15% silicon dioxide (approximately 9.7 MRayl); the matching material 1602 is made from a mixture of approximately 80% copper and approximately 20% silicon dioxide (approximately 7.7 MRayl); the matching material 1603 is made from a mixture of approximately 55% copper and approximately 45% silicon dioxide (approximately 5.9 MRayl); the matching material 1604 is made from a 100% silicon dioxide (approximately 3.8 MRayl); and the matching material 1605 is made from a mixture of approximately 55% acryl and approximately 45% silicon dioxide (approximately 2.0 MRayl).

In any of the cases, the speed of sound is approximately 1800 m/s. Furthermore, the thickness of each of the matching materials 1601 to 1605 is approximately 90 μm.

Figure 17:
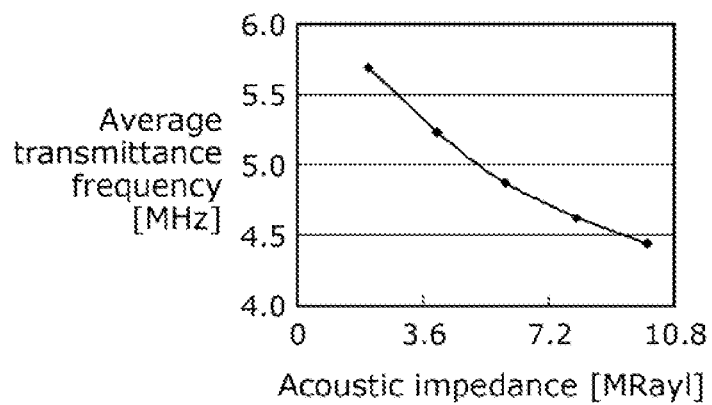
FIG. 17 is a diagram showing a relationship between an acoustic impedance of a multi-impedance layer and an average transmittance frequency of the matching layer.

When it is assumed that the piezoelectric body 208 is the PZT type piezoelectric ceramic (approximately 26 MRayl; speed of sound: approximately 3500 m/s), and the subject has an acoustic impedance of approximately 1.5 MRayl, the average frequency of the ultrasound which is emitted to the subject from the piezoelectric body, reflected off in the subject, and enters the piezoelectric body again (hereinafter referred to as average transmittance frequency) is found to depend on the acoustic impedance of the multi-impedance layer as shown in FIG. 17. It should be noted that the average transmittance frequency is an average in a range less than or equal to 10 MHz.

As shown in FIG. 17, the average transmittance frequency is lower when the acoustic impedance of the multi-impedance layer is larger. it is possible to design the multi-transmittance F characteristic layer by using this characteristics.

Figure 18:
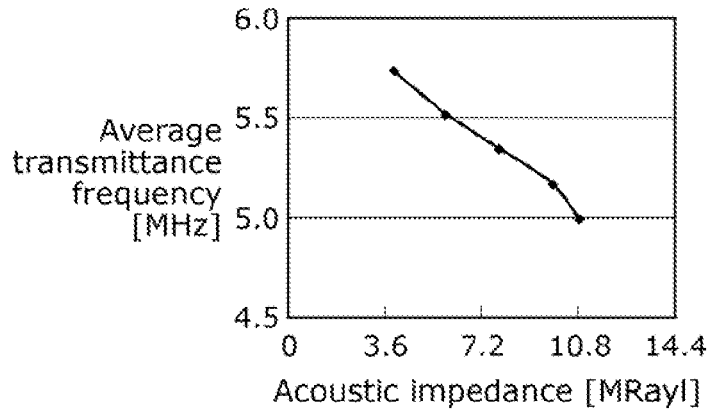
FIG. 18 is a diagram showing a relationship between an acoustic impedance of another multi-impedance layer and an average transmittance frequency of the matching layer.

Furthermore, when the matching layer 1607 is made from a mixture of silver approximately 95% and silicon dioxide approximately 5% (approximately 20 MRayl; thickness: approximately 45 μm), and the thickness of the multi-impedance layer is also 45 μm, the relationship between the acoustic impedance and the average transmittance frequency of the multi-impedance layer is as shown in FIG. 18. Thus, it is indicated that the thickness of the multi-impedance layer and the thickness of the matching layer other than the multi-impedance layer need not necessarily be different.

Furthermore, the above described the matching layer 1606 having two layers in which the multi-impedance layer is on the side of the subject. However, the multi-impedance layer need not necessarily be on the side of the subject.

Figure 19:
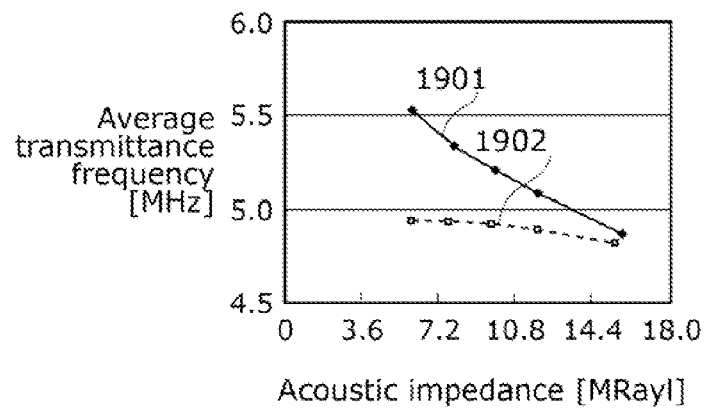
FIG. 19 is a diagram showing a relationship between an acoustic impedance of another multi-impedance layer and an average transmittance frequency of the matching layer.

For example, a solid line 1901 in FIG. 19 shows the relationship between the acoustic impedance and the average transmittance frequency of the multi-impedance layer when the matching layer having a thickness of 90 μm and the acoustic impedance of 2.0 MRayl is provided on the side of the subject, and the multi-impedance layer having the thickness of 45 μm is provided on the side of the piezoelectric body. This relationship can be used to design the multi-transmittance F characteristic layer.

Furthermore, a dotted line 1902 in FIG. 19 shows the relationship between the acoustic impedance and the average transmittance frequency of the multi-impedance layer when the matching layer having a thickness of 90 μm and the acoustic impedance of 3.8 MRayl is provided on the side of the subject, and the multi-impedance layer having the thickness of 45 μm is provided on the side of the piezoelectric body. When both the layer provided on the subject side and the layer provided on the piezoelectric body side are the multi-impedance layers, the adjustable range of average transmittance frequency further increases, and thus it is possible to design the transmittance F characteristic layer more freely. In other words, the above makes it possible to build the ultrasonic diagnostic device with higher S/N and thus is preferable.

Figure 20:
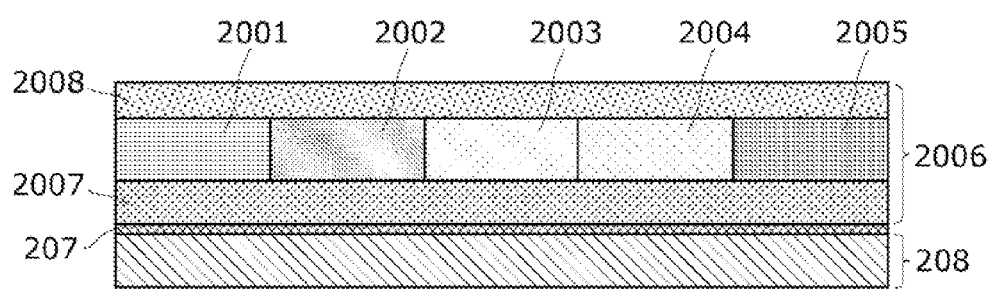
FIG. 20 is a cross-sectional view of another example of the matching layer of the ultrasonic probe according to Embodiment 1 of the present invention.
Figure 20:
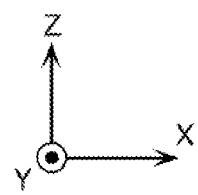

FIG. 20 is a cross-sectional view of another example of the matching layer of the ultrasonic probe according to Embodiment 1 of the present invention. The following describes a matching layer 2006 shown in FIG. 20, which is another example of the multi-transmittance F characteristic layer.

The matching layer 2006 is a three-layer structure matching layer in which a multi-impedance layer (thickness: approximately 45 μm) including five types of matching materials 2001, 2002, 2003, 2004, and 2005 is provided between a matching layer 2007 and a matching layer 2008. The matching layer 2007 is located on the side of the piezoelectric body and is made from a mixture of silver approximately 90% and silicon dioxide approximately 10% (approximately 11.9 MRayl; thickness: approximately 90 μm), and the matching layer 2008 is located on the side of the subject and is made from a mixture of acryl approximately 55% and silicon dioxide approximately 45% (approximately 2.0 MRayl; thickness: approximately 45 μm).

Furthermore, the matching material 2001 is made from a mixture of silver approximately 88% and silicon dioxide approximately 12% (10.8 MRayl), the matching material 2002 is made from a mixture of approximately 85% silver and approximately 15% silicon dioxide (approximately 9.7 MRayl), the matching material 2003 is made from a mixture of approximately 80% copper and approximately 20% silicon dioxide (approximately 7.7 MRayl), the matching material 2004 is made from a mixture of approximately 55% copper and approximately 45% silicon dioxide (approximately 5.9 MRayl), and the matching material 2005 is made from 100% silicon dioxide (approximately 3.8 MRayl).

In any of the cases, the speed of sound is approximately 1800 m/s.

Figure 21:
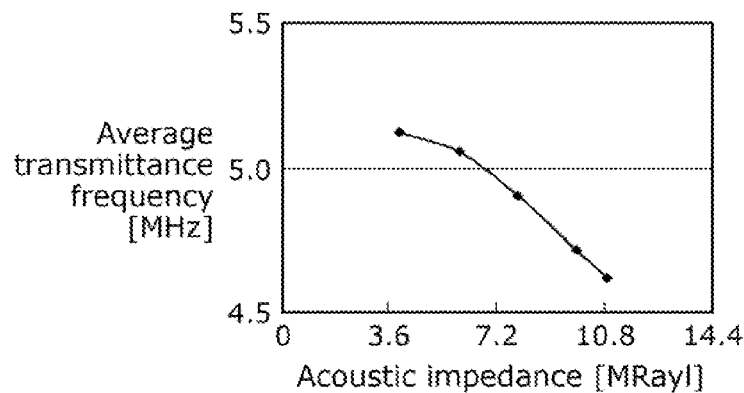
FIG. 21 is a diagram showing a relationship between an acoustic impedance of another multi-impedance layer and an average transmittance frequency of the matching layer.

FIG. 21 shows the relationship between an acoustic impedance and the average transmittance frequency of the multi-impedance layer when the piezoelectric body 208 is the PZT type piezoelectric ceramic (approximately 26 MRayl; speed of sound: approximately 3500 m/s) and the subject has an acoustic impedance of approximately 1.5 MRayl.

In this manner, in the case of the matching layer 2006 in which one layer out of the three layers is the multi-impedance layer as well, it is possible to adjust the average transmittance frequency by changing the acoustic impedance of the multi-impedance layer. Thus, the average transmittance frequency of the multi-transmittance F characteristic layer can be designed.

The above described examples in which at least one layer out of two or three matching layers is the multi-impedance layer. However, it is possible to design the average transmittance frequency by including the multi-impedance layer when the matching layer includes four or more layers as well.

Figure 15:
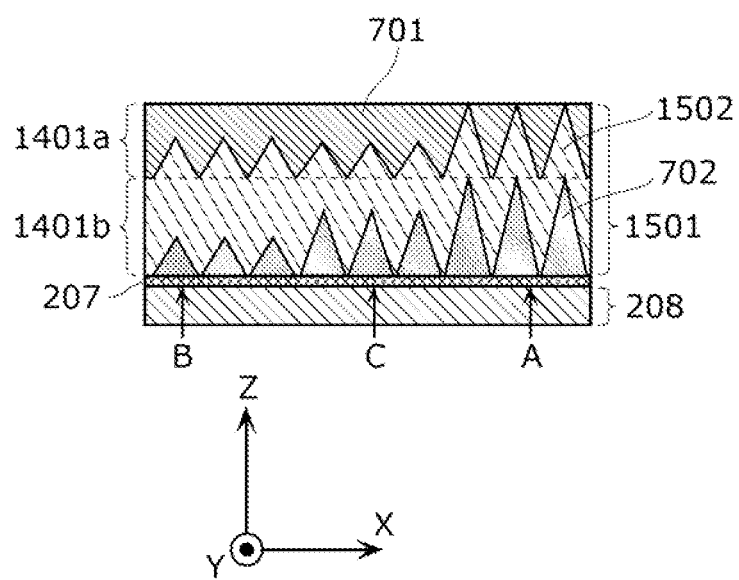
FIG. 15 is a cross-sectional view of another example of the matching layer of the ultrasonic probe according to Embodiment 1 of the present invention.

FIG. 15 is a cross-sectional view of another example of the matching layer of the ultrasonic probe according to Embodiment 1 of the present invention. The following describes a matching layer 1501 shown in FIG. 15, which is another example of the multi-transmittance F characteristic layer.

The matching layer 1501 is a matching layer obtained by stacking two matching layers 1401. Details are as follows. The matching layer 1501 includes: the first matching material 702 having an acoustic impedance close to an acoustic impedance of the piezoelectric body 208; the second matching material 701 having an acoustic impedance close to an acoustic impedance of living body tissue of the subject; and a third matching material 1502 having an acoustic impedance which is smaller than the acoustic impedance of the first matching material 702 and greater than the acoustic impedance of the second matching material 701. The two matching layers 1401 are 1401a and 1401b as shown in FIG. 15. In the 1401a, a plurality of the first matching materials 702 each of which is conical in shape are provided with their bases positioned on the side of the piezoelectric body 208. In the 1401a, the portion other than the portion filled by the first matching materials 702 is filled by the third matching material 1502. Furthermore, in the 1401b which is further above the 1401a (i.e. on the subject side), a plurality of triangular pyramids each of which is made from the third matching material 1502 conical in shape are arranged. The 1401b is formed by filling, with the second matching material 701, the portion other than the portion filled with the third matching material 1502.

In this manner, stacking a plurality of matching layers 1401 makes it possible to design the frequency characteristic of the sound pressure on the surface of the ultrasonic probe more freely, and thus is preferable. With this, it is possible to further enhance S/N in the ultrasonic diagnostic image.

Furthermore, when more than one matching layers 1401 are stacked, it is more preferable that the heights of the cones adjacent to each other are different. With this, the resolution can be further increased. For example, in the example shown in FIG. 15, the height of the cones in the layer 1401b including the first matching material 702 and the third matching material 1502 is as follows: (vicinity of point A)>(vicinity of point C)>(vicinity of point B). On the other hand, the height of the cones in the layer 1401a including the third matching material 1502 and the second matching material 701 is as follows: (vicinity of point A)>(vicinity of point C)≈(vicinity of point B). Furthermore, the heights of the cones in the vicinity of point A are different between the two layers.

Furthermore, the stacking is not limited to the stacking of the matching layers 1401. Stacking the multi-transmittance layer such as the matching layer 703, the matching layer 804, and the matching layer 904, and the multi-transmittance F characteristic layer such as the matching layer 1301, the matching layer 1606, and the matching layer 2006 in combination makes it possible to design the frequency characteristic of the sound pressure more freely, which leads to the increased resolution of the ultrasonic diagnostic image and thus is preferable.

It should be noted that it is preferable that the contact surface between the piezoelectric 101 and the acoustic lens 209 be flat. It should be noted that an error of about 10% with respect to the thickness of the piezoelectric body is acceptable. With this, a high-resolution ultrasonic diagnostic image can be obtained in a wide range of temperature. The reason for this is that acoustic lens has a high rate of shrinkage with respect to a change in temperature. Thus, the acoustic lens may be detached due to shrinkage of the acoustic lens if the contact surface is not flat.

It should be noted that it is preferable that each of the matching sub-layers has a uniform thickness. With this, a high-resolution ultrasonic diagnostic image can be obtained in a wide range of temperature. The reason for this is that the matching sub-layers may be detached from each other due to the variation in rate of shrinkage of the matching sub-layers with respect to the change in temperature of the matching sub-layer if the thickness of each of the matching sub-layers is not uniform.

As described above, the ultrasonic probe according to an aspect of the present invention makes it possible to widen the frequency band of the ultrasound which passes through the matching layer than the conventional matching layer having uniform frequency characteristic. The reason for this is that the ultrasound which passes through the respective matching regions has different frequency characteristic. Thus, when the ultrasound which passed through the respective matching regions is added to the entire matching layer, the frequency band is wider than the frequency band of the ultrasound which passed through the conventional matching layer having a uniform frequency characteristic. Furthermore, the time lag does not occur to the ultrasound pulse which passes through the respective matching regions, because the thickness in the propagation direction of the ultrasound (a predetermined direction) is uniform. As a result, the ultrasound pulse is propagated to the subject in a waveform close to an impulse waveform. Thus, it is possible to obtain a high-resolution ultrasonic diagnostic image.

Furthermore, it is possible to allow the portion of the matching layer close to the piezoelectric body to have an acoustic impedance close to the acoustic impedance of the piezoelectric body, and allow the portion of the matching layer close to the subject to have an acoustic impedance close to the acoustic impedance of the subject. Furthermore, in the matching layer, it is possible to continuously change the acoustic impedance in the propagation direction of the ultrasound.

Furthermore, it is possible to realize the matching regions having different frequency characteristics of ultrasound transmittance. The reason for this is that the matching regions which are different in density of the tapered shapes have different frequency characteristics of ultrasound transmittance.

Furthermore, it is possible to realize the matching regions having different frequency characteristics of ultrasound transmittance. The reason for this is that the matching regions which are different in height, in propagation direction of the ultrasound, of the tapered shapes have different frequency characteristics of ultrasound transmittance.

Furthermore, it is possible to realize the matching regions having different frequency characteristics of ultrasound transmittance. The reason for this is that the matching regions which are different in thickness of the tapered shapes have different frequency characteristics of ultrasound transmittance.

Furthermore, the contact surface between the matching layer and the acoustic lens is flat, and thus the ultrasonic probe can receive, in a wide range of temperature, ultrasound in a wide band. As a result, it is possible to obtain a high-resolution ultrasonic diagnostic image. The reason for this is that acoustic lens has a high rate of shrinkage with respect to the change in temperature. Thus, the acoustic lens may be detached due to shrinkage of the acoustic lens if the contact surface is not flat.

Furthermore, the acoustic matching between the piezoelectric body and the subject can be performed with higher precision, and at the same time, it is possible to widen the frequency band of the ultrasound which passes through the matching layer. The reason for this is that the matching sub-layers having different acoustic impedances make it possible to perform acoustic matching in a stepwise manner from the piezoelectric body to the subject, and the matching regions make it possible to widen the frequency characteristic of ultrasound transmittance.

Furthermore, the ultrasonic probe can receive, in a wide range of temperature, ultrasound in a wide band. As a result, it is possible to obtain a high-resolution ultrasonic diagnostic image. The reason for this is that the matching sub-layers may be detached from each other due to the variation in a rate of shrinkage of the matching sub-layers with respect to the change in temperature of the matching sub-layer if the thickness of each of the matching sub-layers is not uniform.

Furthermore, it is possible to realize the matching layers having different frequency characteristics of ultrasound transmittance. The reason for this is that the matching regions including mixtures which are different in mixture ratio of materials have different frequency characteristic of ultrasound transmittance.

Furthermore, it is possible to realize the matching regions having different frequency characteristics of ultrasound transmittance. The reason for this is that, when the width of the matching region is smaller than the wavelength of the ultrasound, the matching region of which frequency characteristic of ultrasound transmittance is a predetermined value is not formed.

Furthermore, it is possible to efficiently manufacture the matching materials having different densities. The reason for this is that the matching materials having different densities can be manufacture with the same materials by simply changing their mixing ratios.

Furthermore, it is possible to increase the sound pressure of the ultrasound that is propagated toward the direction of the subject from the piezoelectric body.

Furthermore, it is possible to widen the frequency band of the ultrasound which passes through the matching layer.

(Embodiment 2)

Figure 6:
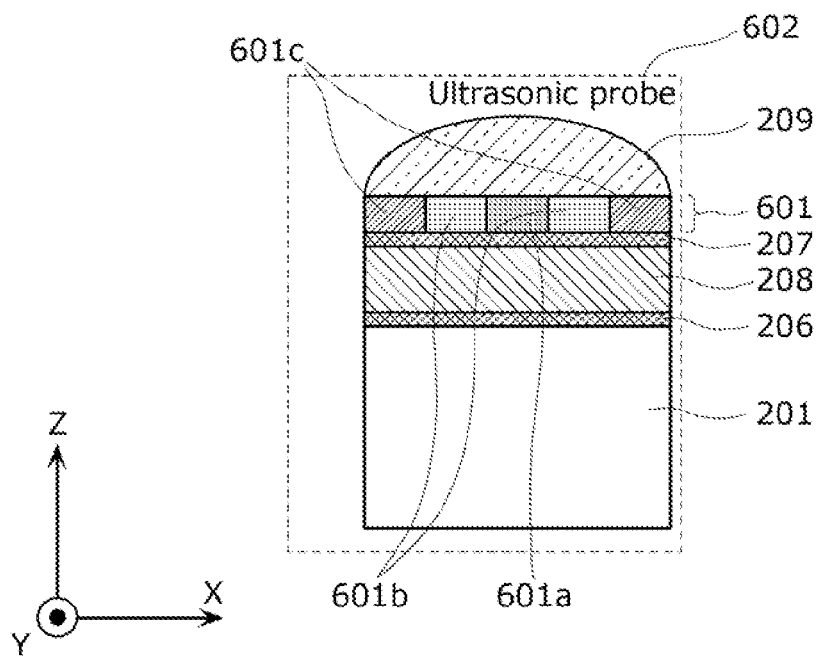
FIG. 6 is a cross-sectional view of an example of an ultrasonic probe according to Embodiment 2 of the present invention.

FIG. 6 is a cross-sectional view of an example of an ultrasonic probe according to this embodiment.

As shown in FIG. 6, an ultrasonic probe 602 of the present invention includes: a piezoelectric body 208; a signal electrode 206; and a ground electrode 207. Furthermore, it is more preferable that the ultrasonic probe 602 include a backing 201, and an acoustic lens 209.

The ultrasonic probe 602 is different from a conventional ultrasonic transducer 304 in that the ultrasonic probe 602 includes a matching layer 601 between the ground electrode 207 and a subject (not shown).

The ultrasonic probe 602 is designed so that the average frequency of the ultrasound emitted from matching regions 601c located at each end in the X-direction (the elongated direction of each of the ultrasonic transducers) of the matching layer 601 is higher than the average frequency of the ultrasound emitted from the matching region 601a located in the center.

This allows the ultrasound having a high frequency, which is suitable by nature for application for focusing, to be further narrowed down and localized, and the ultrasound having low frequency to be propagated broadly. In addition, it is possible to obtain both information regarding the ultrasonic diagnostic image obtained from the localized narrow beam (having a high frequency) and information regarding the ultrasonic diagnostic image obtained from the broad beam (having a low frequency), by isolating and analyzing for each frequency the ultrasound signal reflected off the subject.

The ultrasonic diagnostic image obtained from the broad beam is an image in which reflection and scatter in the region is averaged, Thus, positioning at high speed is possible by using such image for position adjustment. Furthermore, the ultrasound image obtained from the localized narrow beam can provide, in high contrast, the data on reflection and scatter obtained from the localized portion without averaging such data.

It is apparent that the ultrasonic probe according to this embodiment can be designed using the multi-transmittance layer and the multi-transmittance F characteristic layer as described in Embodiment 1, and the descriptions on the structure of the matching layer is omitted here.

The respective features of Embodiment 1 and Embodiment 2 are comparatively described, Embodiment 1 is preferable in that the ultrasonic diagnosis with high S/N can be realized at a low cost. Furthermore, Embodiment 2 is preferable for the application, such as detection of an early carcinoma, which requires more detailed image to make a diagnosis.

Figure 2:
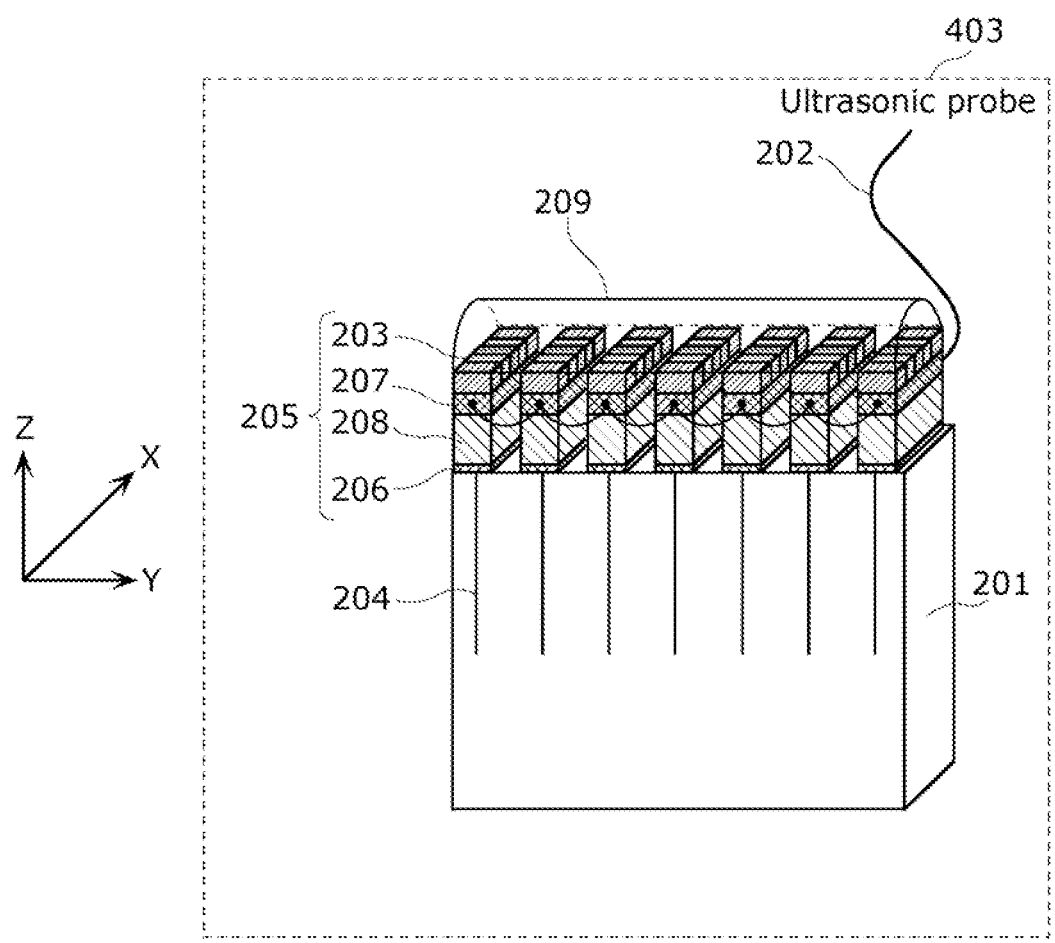
FIG. 2 is a schematic view of an example of a one-dimensional array type ultrasonic probe.

Furthermore, it is preferable that, in the ultrasonic probe in which a plurality of ultrasonic transducers are arranged in a one-dimensional array as shown in FIG. 2, the ultrasonic transducer according to Embodiment 1 and the ultrasonic transducer according to Embodiment 2 are arrange alternately. The reason for this is that characteristics of both of the ultrasonic transducers can be attained, by controlling the respective ultrasonic transducers separately.

Furthermore, following applies to both Embodiments 1 and 2.

In Embodiment 1 and Embodiment 2, examples of the matching layers including matching materials conical in shape and other matching materials that fill the portion between the cones (e.g., FIG. 7, FIG. 8, FIG. 13, FIG. 14, and FIG. 15) have been described. The following applies to the above matching layers.

The matching materials need not necessarily be conical in shape, and may be materials which form at least a depression and a projection. It is more preferable that the matching material be in a shape in which the cross-sectional area continuously decreases from the piezoelectric body toward the subject. For example, the matching material may be in any tapered pillar shape, such as a triangular pyramid shape, a quadrangular pyramid shape, or a campanulate shape. When the height and the width of the depression and the projection of the tapered pillar is different, it is possible to produce advantageous effects similar to the advantageous effects produced by the difference in heights and intervals of the conical shape described in Embodiment 1.

Furthermore, in examples shown in FIG. 7 and FIG. 8, it is preferable that the thickness (in the direction from the piezoelectric body toward the subject) of the matching layer 101 be greater than the half of the wavelength of the ultrasound. This increases the average transmittance of the entire region, and the sensitivity of the ultrasonic probe is further increased. Thus, it is possible to obtain the ultrasonic diagnostic image of the deeper portion of the subject.

Furthermore, the following applies to the multi-impedance layer used in Embodiments 1 and 2.

First, it is preferable that the width of each of the matching regions having different acoustic impedances be greater than the wavelength of the ultrasound generated in the piezoelectric body.

The reason for this is that the difference in the frequency characteristic of transmittance caused by the difference in acoustic impedance within the range equal to or less than the wavelength of the ultrasound is reduced by the diffraction phenomenon of the wave, Designing each of the matching regions to have a width that is greater than the wavelength of the ultrasound generated in the piezoelectric body makes it possible to design the frequency characteristic of the sound pressure more freely, and thus is preferable.

Furthermore, the regions having different acoustic impedances in the multi-impedance layer according to this embodiment are divided by planes perpendicular to the X-direction in FIG. 9. However, the regions need not necessarily be divided by the planes perpendicular to the X-direction, but may be divided by any planes other than the plane perpendicular to the Z-direction.

Furthermore, the matching layer including a mixture of silicon dioxide with copper, silver, and acryl is used in this embodiment, which is merely an example, and it is apparent that other material, such as iron or tungsten, may be used.

The mixture of silicon dioxide with copper, silver, and acryl described in this embodiment significantly changes in the acoustic impedance when the mixing ratio thereof is changed, and has approximately a constant sound speed. Therefore, it is possible to reduce the degradation in picture quality of the ultrasonic diagnostic image caused by the time lag of the ultrasound which passes through the respective matching region. Thus, the above mixtures are preferable for the present invention.

In particular, the mixture of silver and the silicon dioxide allows adjustment of the acoustic impedance in a wide range in a region having a high acoustic impedance for which there are a small number of alternative materials. Thus, it is possible to design the transmittance distribution more freely, and thus the mixture of silver and the silicon dioxide is a preferable material.

Furthermore, a mixture of copper and silicon dioxide allows a wide range of adjustment of the acoustic impedance at a low cost, and thus is preferable.

Furthermore, in the respective range described above, increasing the ratio of silver or copper mixed into silicon dioxide causes density to increase monotonically, and increasing the ratio of acryl mixed into silicon dioxide causes density to decrease monotonically. Thus, the matching layer can be designed easily.

Furthermore, it is preferable that sintering process be performed after forming a film from the matching layer material. In other words, instead of using the matching layer in a state in which the metal particles of silver, copper, and the like are individually dispersed in the binder material, it is preferable that each of the particles be bound and bulked. This makes it possible to obtain a film having higher impedance as well, and increases the flexibility in designing.

Furthermore, it is preferable that the metal mixed into silicon dioxide be metal nano-particles each of which has a diameter below several hundred nanometers. The size of the surface area of the metal nanopowder is such that the metal nanopowder is highly reactive, and a sintering starting temperature varies between 100 and 350 degrees Celsius depending on the diameter of the powder. However, the time to raise and lower the temperature can be reduced with an inexpensive heating unit, and thus the matching layer can be manufactured at a low cost.

Furthermore, although the above described an example in which the silicon dioxide is used as the binder, other inorganic binder, such as titanium oxide or niobium oxide, or organic binder may be used. However, the above-described example which uses the silicon dioxide can increase the change in density while reducing the change in speed of sound, and is inexpensive as well. In view of this the silicon dioxide is an optimal material for the binder of the present invention.

Furthermore, it is preferable that the matching layer in the ultrasonic transducer according to the present invention be a film formed by diluting the material for the matching layer by water or the like, and printing or spraying the diluted material. The concentration of the mixed material can be easily changed for each of the locations by, using a different nozzle for each of the materials, forming a film by printing or spraying. Therefore, the use of printing or spraying is preferable for the present invention because the multi-impedance layer can be formed at a low cost compared to the case in which a method such as the vapor deposition, sputtering, or spin coating is used.

Furthermore, in the multi-impedance layer realized by changing the concentration of the materials for each of the locations (regions) as described above, it is preferable that the adjacent regions include the same material. With this, the adhesion of one of the regions to its adjacent region increases.

This makes it possible to increase the resistance of the ultrasonic transducer to vibration and heat.

Furthermore, when the matching layer including a mixture which includes a plurality of materials as described above is used, it is more preferable that the mixture include materials of which average particle diameters are different by approximately about one digit (different by at least five times). The reason for this is that the mixture which includes materials having different particle diameters makes it possible to reduce, in the regions having different concentrations, the change in the speed of sound that is caused by the change in the mixing ratio of the mixtures.

Furthermore, it is preferable that the matching layer include sintered material.

As above, as the ultrasonic probe and the ultrasonic diagnostic device, Embodiment 1 and Embodiment 2 described the one-dimensional array type ultrasonic probe and the ultrasonic diagnostic device which includes the one-dimensional array type ultrasonic probe. However, each of the configurations described in the embodiments in this DESCRIPTION is merely an example, and it is apparent that various modifications can be made without departing from the essence of the present invention.

In other words, the similar advantageous effects can be produced in the case of the ultrasonic probe with a K31 mode as well. In other words, the ultrasonic diagnostic device of high precision can be realized by providing, on the contact surface between the ultrasonic probe and the subject, a plurality of regions which are different in sound pressure-frequency characteristics of ultrasound.

Furthermore, it is more preferable that the matching layer (not shown) be included between the piezoelectric body 208 and the backing 201. It is preferable that the matching layer between the piezoelectric body 208 and the backing 201 also be the multi-transmittance layer or be the matching layer having different transmittance for each frequency. This makes it possible to reduce the difference in the ultrasound pulse waveform which occurs because Q factor of the ultrasonic transducer including the piezoelectric body 208 is different for each of the regions. In other words, in the region on the side of the subject where the transmittance of the multi-transmittance layer is relatively high, it is preferable that the transmittance of the multi-transmittance layer on the side of the backing 201 be designed relatively low; and, in the region on the side of the subject where the transmittance of the multi-transmittance layer is relatively low, it is preferable that the transmittance of the multi-transmittance layer on the side of the backing 201 be designed relatively high. With this, the difference in the pulse waveforms of ultrasound generated for each of the regions is reduced. Thus, the resolution in the depth of the ultrasonic diagnostic image is increased.

Furthermore, a penetration blocking layer which increases reflectance of the ultrasound may be provided between the piezoelectric body and the backing. With this, the ultrasonic probe having higher sensitivity can be realized. Thus, the ultrasonic diagnosis of deeper portion of the subject can be made.

Furthermore, as the ultrasonic probe which allows designing of sound pressure at the contact surface between the subject and the ultrasonic probe, the method in which different voltage is applied for each of the ultrasonic transducers in the X-direction as well in the two-dimensional array type ultrasonic probe is also possible. However, each of the ultrasonic transducers is thin, and thus leads to a decrease in manufacturing yield and decrease in reliability on drop impact. Furthermore, such method causes an increase in the number of man-hours for manufacturing, and thus increases the costs.

Thus, a method in which the matching layer which creates the transmittance distribution according to the present invention is provided is more preferable.

Furthermore, the two-dimensional array type ultrasonic probe which includes the matching layer having transmittance distribution according to the present invention is even more preferable. This makes it possible to realize the higher S/N with a smaller number of divisions, and thus it is possible to reduce the decrease in manufacturing yield, reduce the decrease in the reliability on drop impact, and reduce the increase in costs due to the increase in the number of man-hours for manufacturing.

Furthermore, for example, the following methods may be used to build the ultrasonic probe in which the sound pressure of the ultrasound decreases, from the center of each of the transducers, toward each of the ends in the X-direction: a method in which processing is performed to provide grooves on ultrasound transducer to form density distribution of the piezoelectric body; a method in which distribution of intensity of polarization is provided; and a method in which the electrode (at least one of the signal electrode and the ground electrode) is made thin, from the center of each of the transducers, toward each of the ends in the X-direction, However, the method in which processing is performed to provide grooves on the ultrasonic transducer causes the manufacturing process to be complicated, and the quality to be unstable. Furthermore, the method in which distribution of intensity of polarization is provided involves a complicated polarization process. Furthermore, the method in which the electrode is made thin, from the center of each of the transducers, toward each of the ends in the X-direction complicates position adjustment between a cut portion and the electrode, and reduces manufacturing yield. Thus, it is preferable that the matching layer shown in this embodiment be used.

Furthermore, as the matching layer which creates the transmittance distribution as with the present invention, for example, a matching layer in which the average particle diameter in the center of each of the ultrasonic transducers is different from the average particle diameter in each of the ends in the X-direction may be used. However, the ultrasound, which scattered in the region including particles of large diameters and having high attenuation, becomes the cause of the noise in the ultrasonic diagnostic image. Thus, the structure described in this embodiment is more preferable.

Figure 4:
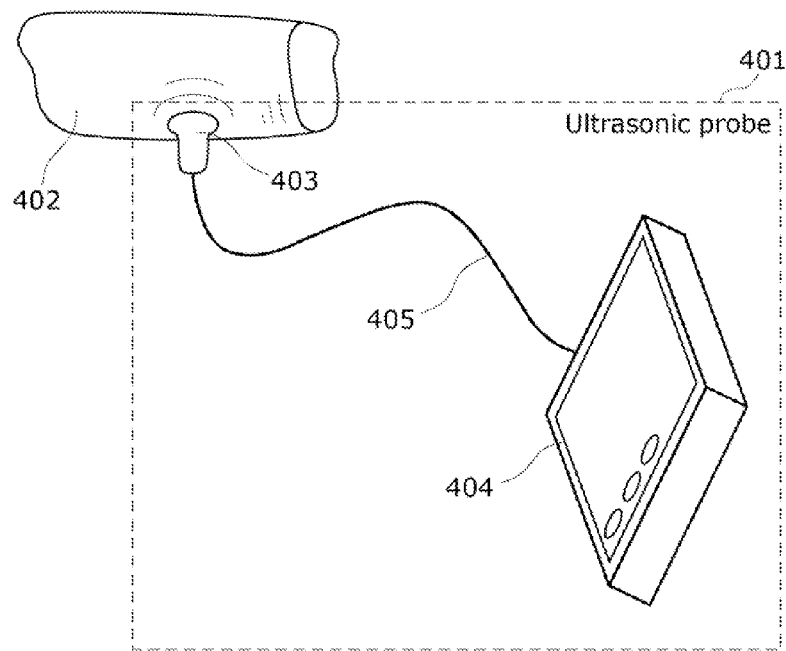
FIG. 4 is an example of a schematic view showing an ultrasonic diagnostic device.

As above, the ultrasonic probe according to the present invention has been described in Embodiment 1 and Embodiment 2. As with the conventional type, the ultrasonic probe is of the one-dimensional array type shown in FIG. 2 or the two-dimensional array type, and is used for the ultrasonic diagnostic device as shown in FIG. 4. This produces the above described advantageous effects such as enhanced S/N.

(Embodiment 3)

This embodiment describes an ultrasonic transducer which includes a matching layer including a plurality of matching regions having different densities.

Figure 22:
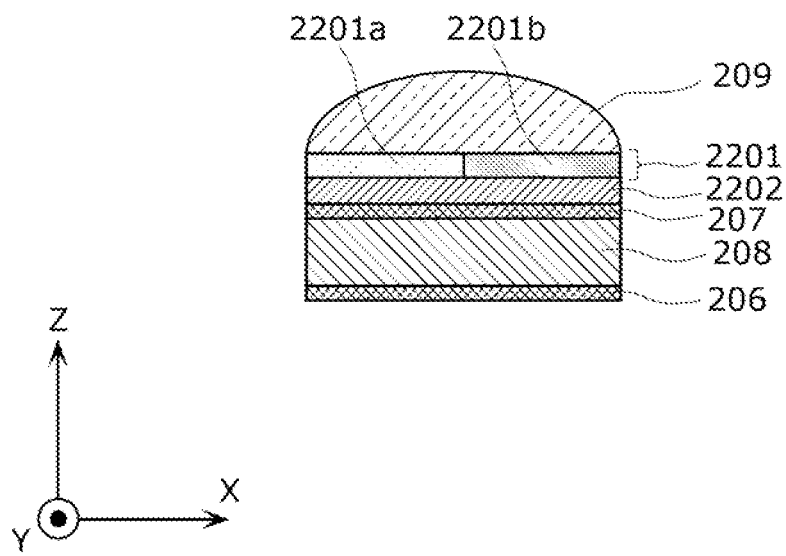
FIG. 22 is an example of a cross-sectional view of an ultrasonic transducer according to Embodiment 3 of the present invention.

FIG. 22 is a cross-sectional view of an example of an ultrasonic transducer according to this embodiment.

The ultrasonic transducer shown in FIG. 22 includes: a piezoelectric body 102; and drive electrodes 206 and 207 formed on a pair of opposing surfaces of the piezoelectric body. This makes it possible for the ultrasonic transducer to transmit and receive ultrasound. Furthermore, the ultrasonic transducer Includes matching layers 2201 and 2202 to transmit to and receive from a subject, in an efficient manner, ultrasound generated by the piezoelectric body 208 and the drive electrodes 206 and 207. Furthermore, the ultrasonic transducer includes, between the matching layer 2202 and the subject, an acoustic lens 209 which narrows the ultrasound beam so that the resolution of the diagnostic image is increased.

The matching layer 2201 includes two matching regions 2201a and 2201b having different densities. Furthermore, here, the matching regions 2201a and 2201b are divided by a plane parallel to the Z-direction in which the ultrasound propagates.

The inventors of the present invention conducted dedicated studies and found that the matching layer including a plurality of matching regions having different densities can be obtained as follows.

FIG. 22 is a cross-sectional view of an example of an ultrasonic probe according to this embodiment of the present invention.

Regarding the ultrasonic transducer shown in shown FIG. 22, the piezoelectric body 208 is a PZT type piezoelectric ceramic (density: approximately 7.4 g/cc; speed of sound: approximately 3500 m/s). The drive electrodes 206 and 207 are formed by baking silver onto a pair of opposing surfaces of the piezoelectric body 208.

Furthermore, the matching layer 2202 is made from a mixture of silver approximately 90% and silicon dioxide approximately 10% (density:

approximately 6.6 Wm; thickness: approximately 45 μm), the matching region 2201a of the matching layer 2201 is made from a mixture of silver approximately 85% and silicon dioxide approximately 15% (density: approximately 5.4 g/cc; thickness; approximately 90 μm; speed of sound: approximately 1800 m/s), the matching region 2201b of the matching layer 2201 is made from a mixture of approximately 55% acryl and approximately 45% silicon dioxide (density: approximately 1.1 g/cc; thickness: approximately 90 μm; speed of sound: approximately 1800m/s).

Furthermore, the acoustic lens 209 is made of a silicone rubber (density; approximately 1.5 g/cc; speed of sound: approximately 947 m/s) having an acoustic impedance close to a living body.

Figure 24:
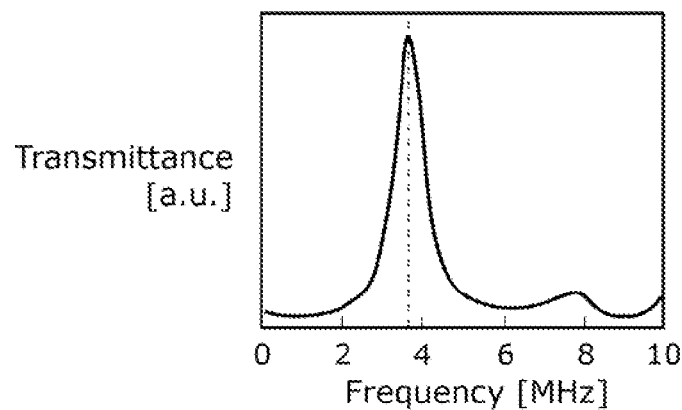
FIG. 24 is a diagram showing transmittance characteristics of a matching layer according to Embodiment 3 of the present invention.

FIG. 24 is a diagram showing transmittance characteristics of the matching layer according to Embodiment 3 of the present invention.

FIG. 24 shows square of transmittance with respect to the respective frequency (hereinafter referred to as transmittance characteristics) of the matching layers 2201 and 2202 of the ultrasonic transducer having the above structure, The square of the transmittance is shown here because the ultrasound travels between the piezoelectric body and the subject when a diagnosis is made with the ultrasonic transducer, and thus the ultrasound passes through the matching layer twice.

Figure 25:
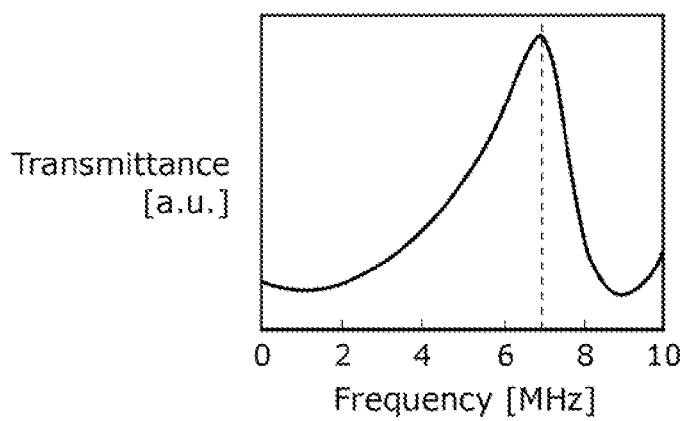
FIG. 25 is a diagram showing transmittance characteristics of another matching layer according to Embodiment 3 of the present invention.

More specifically, FIG. 24 shows transmittance characteristics of the matching layer 2202 and the region 2201a of the matching layer 2201, and FIG. 25 shows a transmittance characteristics of the matching layer 2202 and the region 2201b of the matching layer 2201.

FIG. 25 shows that the two regions have significantly different transmittance properties. In FIG. 24, the peak frequency at which the transmittance is highest is approximately 4 MHz, and the peak frequency in FIG. 25 is approximately 7 MHz.

In this manner, it is found that, when two matching regions are included, it is possible to change the frequency of the transmitted ultrasound by changing the density of at lest one of the matching layers. (Hereinafter, the (matching) layer including a plurality of regions having different density, such as the matching layer 101, is referred to as a "multi-density layer".)

Furthermore, FIG. 24 shows the transmittance characteristics of the case where the multi-density layer has two types of densities which are 5.4 g/cc and 1.1 g/cc. In the same manner, the transmittance characteristics of the case where the ultrasonic transducer has the structure shown in FIG. 22, and the multi-density layer is as follows is evaluated, and the relationship between the density of the multi-density layer and the average transmittance frequency is examined, the result of which is shown in FIG. 27.

(1) (A mixture of silver approximately 85% and silicon dioxide approximately 15% (density: approximately 5.4 (Yee): 101*a*)
(2) A mixture of copper approximately 80% and silicon dioxide approximately 20% (density: approximately 4.3 g/cc)
(3) A mixture of copper approximately 55% and silicon dioxide approximately 45% (density: approximately 3.3 g/cc)
(4) Silicon dioxide 100% (density: approximately 2.1 g/cc)
(5) (A mixture of acryl approximately 55% and silicon dioxide approximately 45% (density: approximately 1.1 g/cc): 101*b*)

The speed of sound is approximately 1800 m/s in any of the cases. Furthermore, the thickness is approximately 90 μm.

Figure 27:
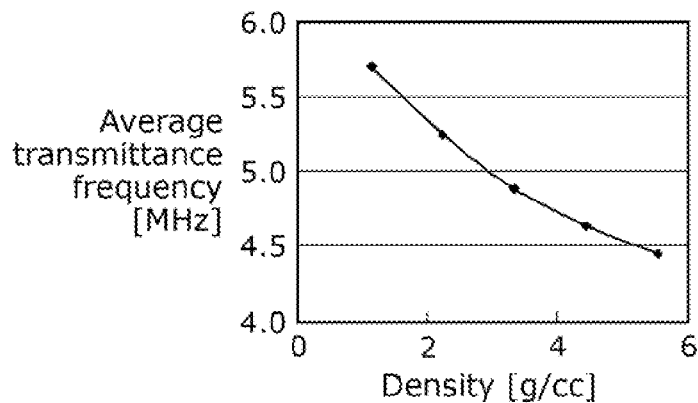
FIG. 27 is a diagram showing a relationship between an average transmittance frequency of the matching layer and a density of a multi-density layer according to Embodiment 3 of the present invention.

FIG. 27 shows that an increase in density of the multi-density layer causes decrease in the average transmittance frequency in the case of the structure according to this embodiment.

Furthermore, the above described the example in which the thickness of the matching layer 105 is 45 μm, and the thickness of the matching layer 101 is 90 μm (speed of sound of each of the layers is approximately 1800 m/s). However, embodiments of the present invention are not limited to the thickness of the respective matching layers, but the advantageous effect of widening the band is produced.

Figure 26:
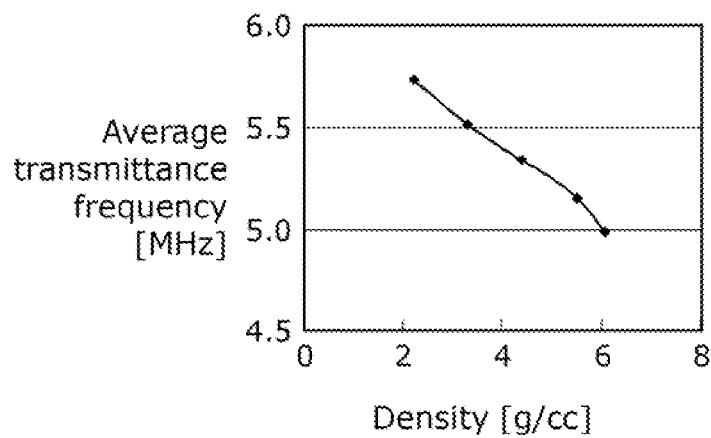
FIG. 26 is a diagram showing a relationship between an average transmittance frequency of two matching layers and a density of a multi-density layer.

For example, FIG. 26 shows a relationship between the density of the matching layer 2201 and the average frequency of the ultrasound which passes through the two matching layers, when both the matching layers 2201 and 2202 have a thickness of 45 μm. As FIG. 26 shows, in the case where the two matching layers have the same thickness as well, the increase in the density of the multi-density layer causes decrease in the average transmittance frequency. Here, FIG. 26 is a diagram showing, as an example, a relationship of the case where the matching layer 2202 is made from a mixture of silver approximately 95% and silicon dioxide approximately 5% (density: approximately 8.6 g/cc).

As described above, the ultrasonic probe according to an aspect of the present invention makes it possible to obtain the matching regions having different frequency characteristic of ultrasound transmittance. The reason for this is that the matching regions having different densities have different frequency characteristics of ultrasound transmittance.

(Embodiment 4)

Figure 30:
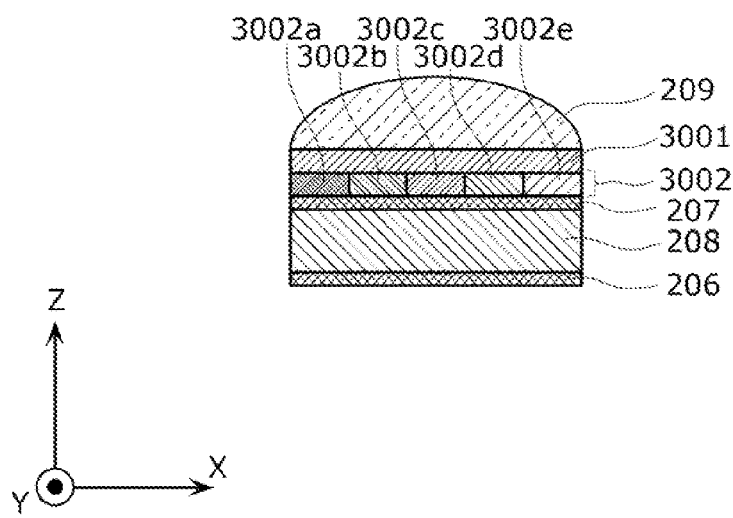
FIG. 30 is a cross-sectional view of an ultrasonic transducer according to Embodiment 4 of the present invention.

FIG. 30 is a schematic cross-sectional view of an example of an ultrasonic transducer according to this embodiment.

As with the ultrasonic transducer of Embodiment 3 shown in FIG. 22, an ultrasonic transducer shown in FIG. 30 includes: a piezoelectric body 208; drive electrodes 206 and 207 that are formed on a pair of opposing surfaces of the piezoelectric body 208; two matching layers, and an acoustic lens 209. The two matching layers are matching layers 3001 and 3002, and the matching layer 3002 is a multi-density layer.

Specifically, out of the two matching layers, the layer on the side of the subject is the multi-density layer in Embodiment 3. In contrast, out of the two matching layers, the layer on the side of the piezoelectric body 208 is the multi-density layer in this embodiment.

The inventors of the present invention conducted dedicated studies and found that the two matching layers including the above-described multi-density layer can be realized as follows.

In this embodiment, the matching layer 3001 is made from a mixture of acryl approximately 55% and silicon dioxide approximately 45% (density: approximately 1.1 g/cc; thickness; approximately 90 μm).
In the matching layer 3002, a matching region 3002*a* is made from a mixture of silver approximately 95% and silicon dioxide approximately 5% (density; approximately 8.6 g/cc; thickness; approximately 45 μm), a matching region 3002*b* is made from a mixture of silver approximately 90% and silicon dioxide approximately 10% (density: approximately 6.6 g/cc; thickness: approximately 45 μm), a matching region 3002*c* is made from a mixture of silver approximately 85% and silicon dioxide approximately 15% (density; approximately 5.4 g/cc; thickness: approximately 45 μm), a matching region 3002*d* is made from a mixture of approximately 80% copper and approximately 20% silicon dioxide (density: approximately 4.3 g/cc; thickness: approximately 45 μm), and a matching region 3002*e* is made from a mixture of approximately 55% copper and approximately 45% silicon dioxide (density: approximately 3.3 g/cc; thickness: approximately 45 μm).

Furthermore, the speed of sound is approximately 1800 m/s in any of the regions.

With the above-described structure, the average transmittance ⁻10 frequency of each of the regions of the multi-density layer (the matching layer 3002) is obtained. The relationship between the density of the multi-density layer (the matching layer 3002) and the average transmittance frequency of the two matching layers is indicated by a solid line 3101 in FIG. 31.

Figure 31:
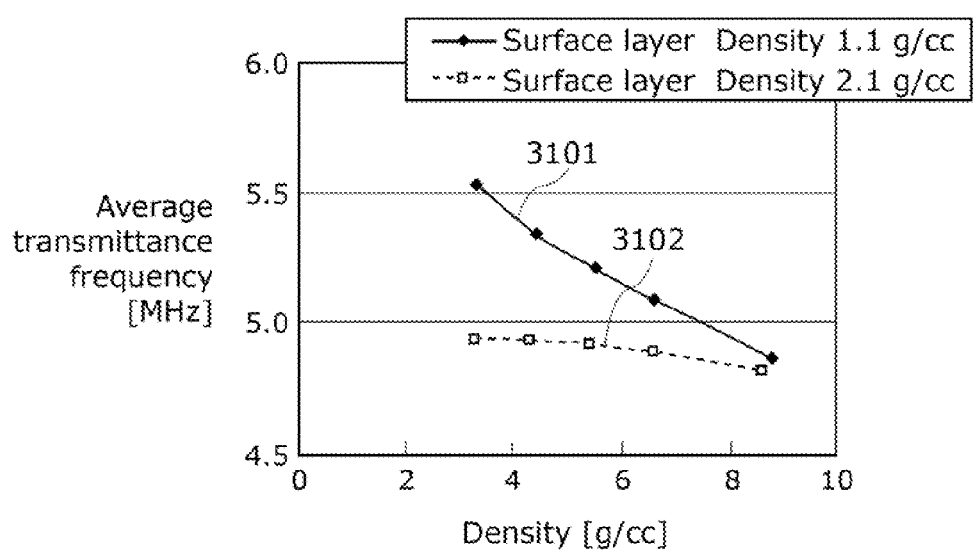
FIG. 31 is a diagram showing a relationship between an average transmittance frequency of a matching layer and a density of a multi-density layer according to Embodiment 4 of the present invention.

FIG. 31 shows that the greater the density of the multi-density layer is, the lower the average transmittance frequency is.

Figure 23:
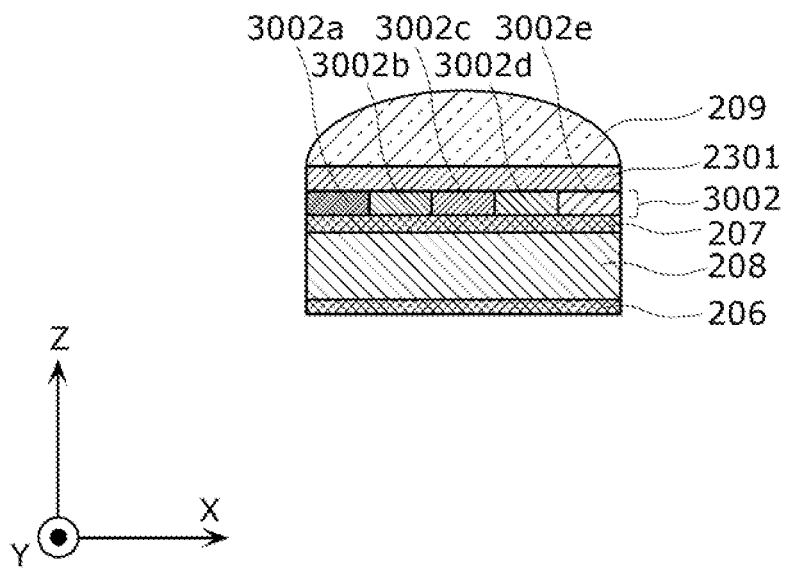
FIG. 23 is a cross-sectional view of an ultrasonic transducer according to Embodiment 4 of the present invention.

Furthermore, a dotted line 3102 in FIG. 31 shows a relationship between the density of the matching layer 3002 and the average transmittance frequency of the two matching layers, when the matching layer on the side of the body (the matching layer 3001 in FIG. 30) is, as shown in FIG. 23, a matching layer 2301 made from 100% silicon dioxide (density: approximately 2.1 g/cc; thickness: approximately 90 μm).

The average transmittance frequency changes when the density of the matching layer 3001 changes, even when the density of the matching layer 3002 is the same. In other words, it has been found that the bandwidth that can be realized can be widen (wider band can be realized) when the ultrasonic probe includes two matching layers both of which are the multi-density layers.

Therefore, compared to the ultrasonic transducer including a plurality of matching layers one of which is the multi-density layer, the ultrasonic transducer including a plurality of multi-density layers can further widen the band, and thus is preferable.

It has been found from Embodiment 3 and Embodiment 4 that the ultrasonic probe which includes two matching layers one of which is the multi-density layer can transmit and receive ultrasound of various frequency without changing the thickness of the matching layer, and thus it is possible to realize a wide band ultrasonic transducer.

(Embodiment 5)

Figure 32:
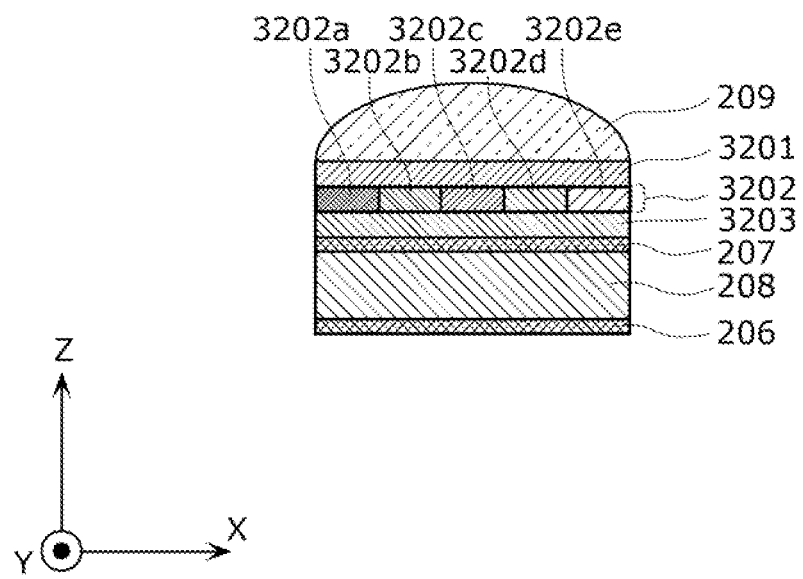
FIG. 32 is a cross-sectional view of an ultrasonic transducer according to Embodiment 5 of the present invention.

The following describes with reference to FIG. 32 an example in which the ultrasonic probe includes three matching layers, and at least one of the three matching layers is a multi-density layer.

The inventors of the present invention conducted dedicated studies and found that the three matching layers, at least one of which is the multi-density layer, can be realized as follows.

As with the ultrasonic transducer in Embodiment 3, the ultrasonic transducer shown in FIG. 32 includes: a piezoelectric body 208; drive electrodes 206 and 207 formed on a pair of opposing surfaces of the piezoelectric body 208; a matching layer, and an acoustic lens 209.

The matching layer included in the ultrasonic transducer shown in FIG. 32 includes three matching layers. A matching layer 3201 is made from a mixture of approximately 55% acryl and approximately 45% silicon dioxide (density: approximately 1.1 g/cc; thickness; approximately 45 μm), and a matching layer 3203 is made from a mixture of approximately 90% silver and approximately 10% silicon dioxide (density: approximately 6.6 g/cc; thickness: approximately 90 μm).

Furthermore, a matching layer 3202 is a multi-density layer, and a matching region 3202a is made from a mixture of approximately 88% silver and approximately 12% silicon dioxide (density: approximately 6.0 g/cc; thickness: approximately 45 μm), a matching region 3202b is made from a mixture of approximately 85% silver and approximately 15% silicon dioxide (density: approximately 5.4 g/cc; thickness: approximately 45 μm), a matching region 3202c is made from a mixture of approximately 80% copper and approximately 20% silicon dioxide (density: approximately 4.3 g/cc; thickness: approximately 45 μm), a matching region 3202d is made from a mixture of approximately 55% copper and approximately 45% silicon dioxide (density: approximately 3.3 g/cc; thickness: approximately 45 μm), and a matching region 3202e is made from approximately 100% silicon dioxide (density: approximately 2.1 g/cc; thickness: approximately 45 μm).

Furthermore, the speed of sound is approximately 1800 m/s in any of the regions.

With the above-described structure, the average transmittance frequency of each of the regions of the multi-density layer (matching layer 3202) is obtained. A solid line 3301 in FIG. 33 shows the relationship between the density of the multi-density layer (the matching layer 3202) and the average transmittance frequency of the three matching layers.

Figure 33:
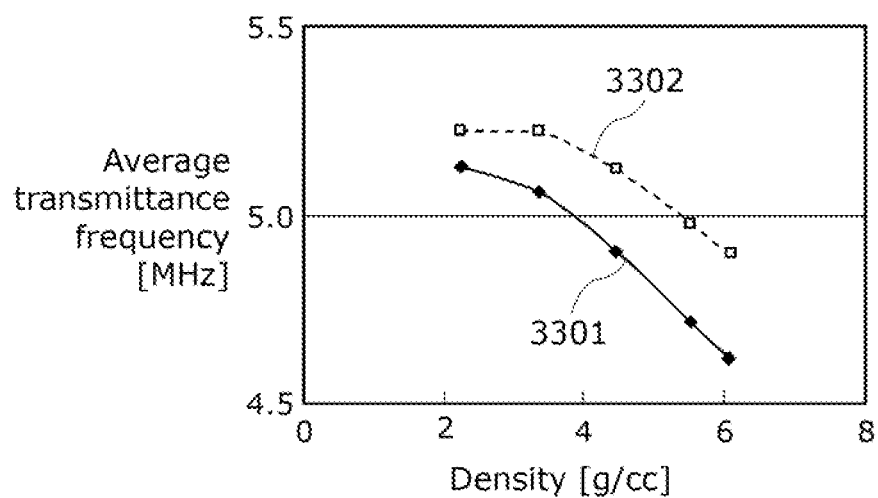
FIG. 33 is a diagram showing a relationship between an average transmittance frequency of a matching layer and a density of a multi-density layer according to Embodiment 5 of the present invention.

FIG. 33 shows that that the greater the density of the multi-density layer is, the lower the average transmittance frequency is.

Figure 34:
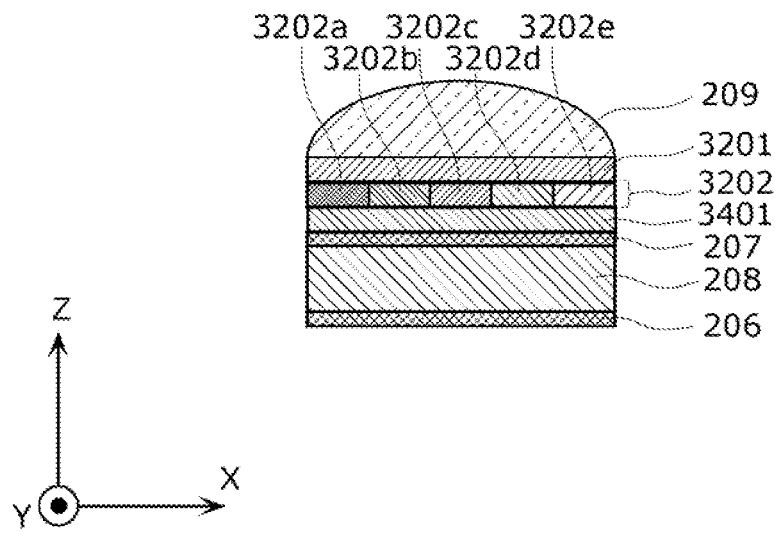
FIG. 34 is a cross-sectional view of another ultrasonic transducer according to Embodiment 5 of the present invention.

Furthermore, a dotted line 3302 in FIG. 33 shows a relationship between the density of the matching layer 3202 and the average transmittance frequency of the three matching layers, when the matching layer on the side of the piezoelectric body (the matching layer 3203 in FIG. 32) is, as shown in FIG. 34, the matching layer 3401 made from a mixture of approximately 95% silver and 5% silicon dioxide.

This indicates that, even when the density of the matching layer 3202 is the same, the average transmittance frequency changes when the density of the matching layer 3203 changes. In other words, it is indicated that the bandwidth that can be realized can be widen (wider band can be realized) when the ultrasonic transducer includes three matching layers two of which are the multi-density layers, compared to the ultrasonic transducer including three matching layers only one of which is the multi-density layer.

In other words, as with Embodiment 4, the ultrasonic transducer including three matching layers can widen the band as well by including a plurality of multi-density layers, and thus is preferable.

It should be noted that the following applies to Embodiments 3 to 5.

Although Embodiments 3 to 5 described the ultrasonic transducer including two or three matching layers, the ultrasonic transducer including four or more matching layers or including one matching layer can also produce the advantageous effects of the present invention, when at least one of the matching layers is the multi-density layer. However, compared to the ultrasonic transducer including one matching layer (i.e. including only the multi-density layer), the ultrasonic transducer including two or more matching layers, at least one of which is the multi-density layer, produces significantly increased effect in widening the band. Therefore, it is preferable that the ultrasonic transducer include two or more matching layers and at least one of the matching layers be the multi-density layer.

Figure 28:
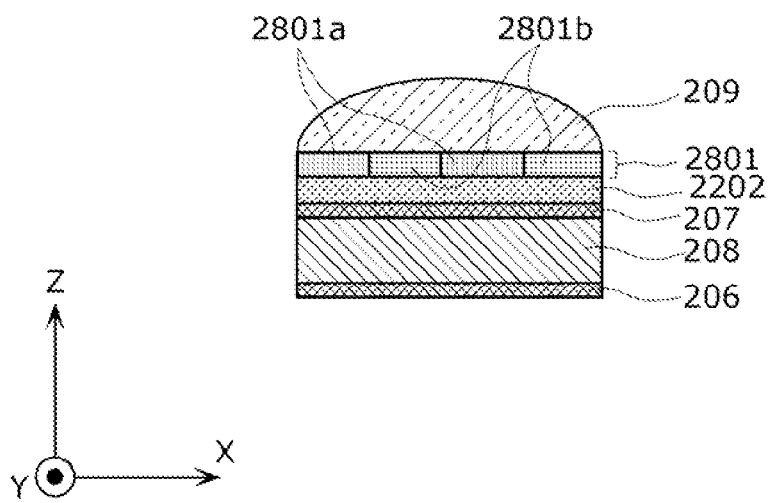
FIG. 28 is a cross-sectional view of another ultrasonic transducer according to Embodiment 3 of the present invention.

Furthermore, Embodiments 3 to 5 described the multi-density layer as a layer which includes regions having different densities each of which is different from each other. However, as FIG. 28 shows another embodiment of Embodiment 3, the ultrasonic transducer may include two or more regions having the same density as a matching layer 2801 shows. Providing the regions having the same density at a plurality of positions makes it possible to further reduce frequency dependency of the ultrasound beam shape in the subject body, and the resolution of the ultrasound beam scan direction (the X-direction and the V-direction) can be increased, and thus is preferable.

Furthermore, in the multi-density layer included in the ultrasonic transducer according to the present invention, it is preferable that the width of each of the regions (a region width at least in one direction) having a different density be greater than the wavelength of the ultrasound generated in the piezoelectric body.

This is because a part of the effect in widening the band produced by the change in density less than or equal to the wavelength of the ultrasound is canceled by the diffraction phenomenon of waves. Increasing the width of each of the regions to be greater than the wavelength of the ultrasound generated in the piezoelectric body makes it possible to produce greater effects in widening frequency band, and thus is more preferable.

Figure 29:
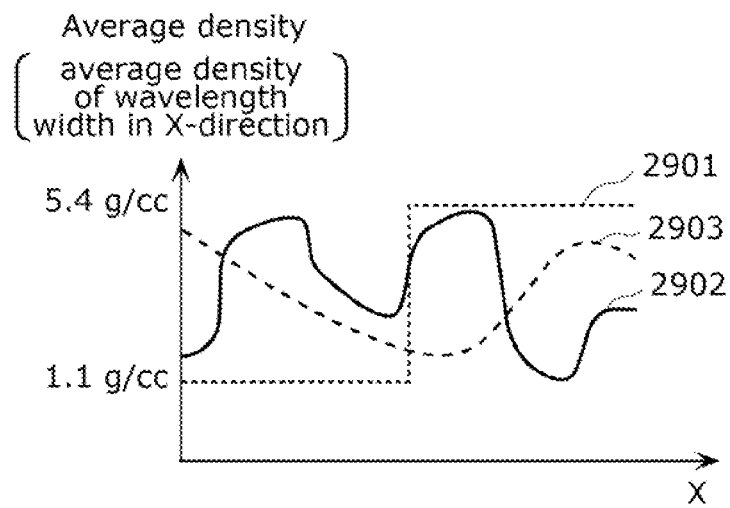
FIG. 29 is a diagram showing an example of a relationship between a position (in an axis perpendicular to a propagation direction of ultrasound) and an average density of a multi-density layer.

Furthermore, FIG. 29 shows an example of the density distribution of the multi-density layer. Here, the horizontal axis indicates the X-direction. However, the horizontal axis may indicate any direction perpendicular (in the XY-plane) to the Z-direction. Furthermore, due to the aforementioned reason (the density change in the region having wider width than the wavelength can produce greater effects for widening the band), the vertical axis indicates the average density of the region having the same length (of the horizontal axis: here, of the X-direction) as the wavelength of the ultrasound. For example, the density distribution of a matching layer 2201 is shown in FIG. 29, and is divided into two portions which are a portion of 1.1 g/cc and a portion of 5.4 g/cc as indicated by a dotted line 2901.

However, for example, even in the case of the multi-density layer in which the density continuously changes as shown by a solid line 2902 and a broken line 2903, great effects are produced in widening the band and thus advantageous effect of the present invention is produced as long as the density averaged in the region having the width about the same as the wavelength of the ultrasound changes depending on the location in the multi-density layer.

Furthermore, regions (a region 2201*a* and a region 2201*b*) having different densities in the multi-density layer of this embodiment is divided by a plane perpendicular to the Y-direction in FIG. 22. However, the regions need not necessarily be divided by the plane perpendicular to the Y-direction, but may be divided by any planes other than the plane perpendicular to the Z-direction.

Furthermore, this embodiment used the matching layers each of which includes a mixture of silicon dioxide and one of copper, silver, or acryl. However, each of such matching layers is merely an example, and it is apparent that other material, such as iron or tungsten, may be used.

However, the mixture of silicon dioxide and one of copper, silver, and acryl has, when the mixing ratio thereof is changed, a great change in density and a substantially constant speed of sound, which makes it possible to reduce degradation of picture quality of the ultrasonic diagnostic image caused by the time lag of the ultrasound which passes through each of the regions, and thus is a preferable material for the present invention.

In particular, for example, when the ratio of silver mixed into silicon dioxide is set to an arbitrary ratio in a range from 0 to 99%, it is possible to realize an arbitrary density in a wide range of approximately 2.2 to approximately 8.6 g/cc. Mixing silver and changing the concentration of silver for each of the locations increases the effects in widening the band, Furthermore, for example, when the ratio of copper mixed into silicon dioxide is set to an arbitrary ratio in a range from 0 to 90%, it is possible to realize an arbitrary density in a range from approximately 2.2 to approximately 5.6 g/cc. In addition, the matching layer can be realized at a significantly low cost, and thus the use of copper is preferable.

Furthermore, for example, when the ratio of acryl mixed into silicon dioxide is set to an arbitrary ratio in a range from 0 to 55%, it is possible to realize an arbitrary density in a range from approximately 2.2 to approximately 1.1 g/cc. Thus, the use of acryl is preferable, In the respective range described above, increasing the ratio of silver or copper mixed into silicon dioxide causes density to increase monotonically, and increasing the ratio of acryl mixed into silicon dioxide causes density to decrease monotonically, Thus, the matching layer can be designed easily.

Furthermore, it is preferable that sintering process be performed after forming a film from the matching layer material. In other words, instead of using the matching layer in a state in which the metal particles of silver, copper, and the like are individually dispersed in the binder material, it is preferable that each of the particles be bound and bulked. This makes it possible to obtain a film having higher impedance, and increases the effect in widening the band as well.

Furthermore, it is preferable that the metal mixed into silicon dioxide be metal nano-particles each of which has a diameter below several hundred nanometers. The size of the surface area of the metal nanoparticle is such that the metal nanopparticle is highly reactive, and a sintering starting temperature varies between 100 and 350 degrees Celsius depending on the diameter of the particles. However, the time to raise and lower the temperature can be reduced with an inexpensive heating unit, and thus the matching layer can be manufactured at a low cost.

Furthermore, although the above described an example in which the silicon dioxide is used as the binder, other inorganic binder, such as titanium oxide or niobium oxide, or organic binder may be used. However, the above-described example which uses the silicon dioxide can increase the change in density while reducing the change in speed of sound, and is also inexpensive. In view of this, the silicon dioxide is an optimal material for the binder of the present invention.

Furthermore, it is preferable that the matching layer in the ultrasonic transducer according to the present invention be a film formed by diluting the material for the matching layer by water or the like, and printing or spraying the diluted material. The concentration of the mixed material can be easily changed for each of the locations by, using a different nozzle for each of the materials, forming a film by printing or spraying, and the use of printing or spraying is preferable for the present invention because the multi-impedance layer can be formed at a low cost compared to the case in which a method such as the vapor deposition, sputtering, or spin coating is used.

Furthermore, it is preferable that the adjacent regions in the multi-density layer, which is realized by changing the concentration of the materials for each location (matching region) as described above, include the same material. With this, the adhesion of one of the matching regions to its adjacent matching region increases, and thus vibration resistance property and heat resistance property of the ultrasonic transducer increases.

Furthermore, when the matching layer including a mixture which includes a plurality of materials as described above is used, it is more preferable that the mixture include materials of which average particle diameters are different by approximately about one digit (different by at least five times). When the mixture includes materials of which particle diameters are different, it is possible to maintain the speed of sound approximately constant in regions having different concentrations.

When the thickness or the speed of sound is also different in the regions which have different densities in the multi-density layer, a problem of degradation in the ultrasound waveform occurs because of the time lag of ultrasound passing through the each of the regions as described above. However, greater effects are produced in widening the band. Thus, the multi-density layer may include regions in which both density and one of thickness and speed of sound are different may be adopted. In other words, the multi-density layer may be combined with the conventional example (patent literature 1).

According to the present invention, density is also different. Thus, it is possible to widen the band with less change in speed of sound and thickness compared to the conventional example. Thus, it is possible to widen the band while reducing the degradation in ultrasound waveform than when the conventional example is used without any modifications.

When speed of sound or thickness is different in regions of the multi-density layer, it is preferable that the time lag of the ultrasound passing through each of the matching regions be ¼ or less of a cycle of ultrasound. This is because the above makes it possible to reduce degradation in resolution caused by degradation in the ultrasound waveform.

(Embodiment 6)

This embodiment describes an ultrasonic diagnostic device which includes the ultrasonic transducer described in Embodiments 3 to 5.

FIG. 4 shows a structure of the ultrasonic diagnostic device according to this embodiment. Note that an ultrasonic probe 403 has the structure shown in FIG. 2. The ultrasonic probe 403 includes an ultrasonic transducer described in Embodiments 3 to 5.

A signal electrode 206 and a ground electrode 207 are formed on a pair of opposing surfaces of the piezoelectric body 208. A plurality of the piezoelectric bodies 208 are boned, via the surface on which the signal lines 206 are formed, to a backing material 201 to form a one-dimensional array. The backing material 201 absorbs unnecessary sound waves.

A matching layer 203 is provided on the +Z side of the piezoelectric body 208, an acoustic lens 209 is provided on the +Z side of the matching layer 203, and the ultrasonic probe 403 emits ultrasound to a subject (not shown) through the acoustic lens.

Here, the matching layer 203 includes the multi-density layer, as described in Embodiments 3 to 5.

The ultrasonic probe including the ultrasonic transducer (the ultrasonic transducer including the matching layer which includes the multi-density layer) described in Embodiments 3 to 5 makes it possible to transmit and receive ultrasound in wider band. With this, it is possible to make a ultrasonic diagnosis in high resolution.

Figure 35:
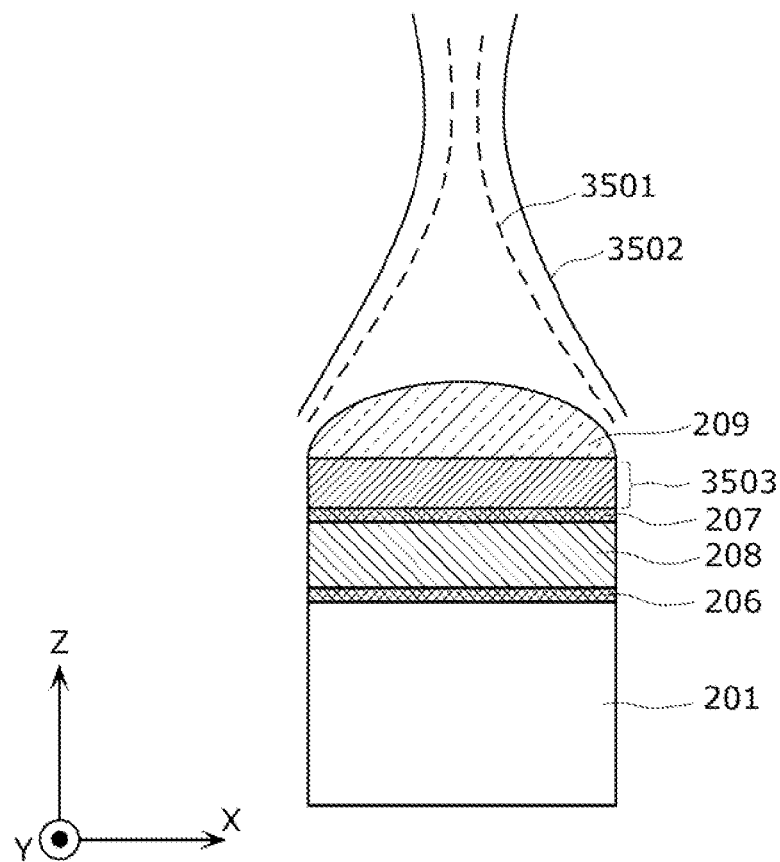
FIG. 35 is a schematic view showing a conventional ultrasonic probe and propagation of ultrasound.

Furthermore, normally, as shown in FIG. 35, when the ultrasound emitted from the ultrasonic transducer including a matching layer 3503 which does not include the multi-density layer is focused using one acoustic lens, the focusing effect is higher on the ultrasound having a higher frequency and thus the ultrasound can be narrowed to be thin as shown by a dotted line 3501 shown in FIG. 35, but the focusing effect is weaker on ultrasound having lower frequency and thus ultrasound results in a broad beam as indicated by a solid line 3502.

The ultrasound beams which propagates, as the ultrasound beam having a different thickness depending on the frequency, in the body of the subject as described above results in the ultrasound pulse which has a different waveform according to the location inside the body of the subject. This causes the degradation of picture quality of the ultrasonic diagnostic image.

Figure 36:
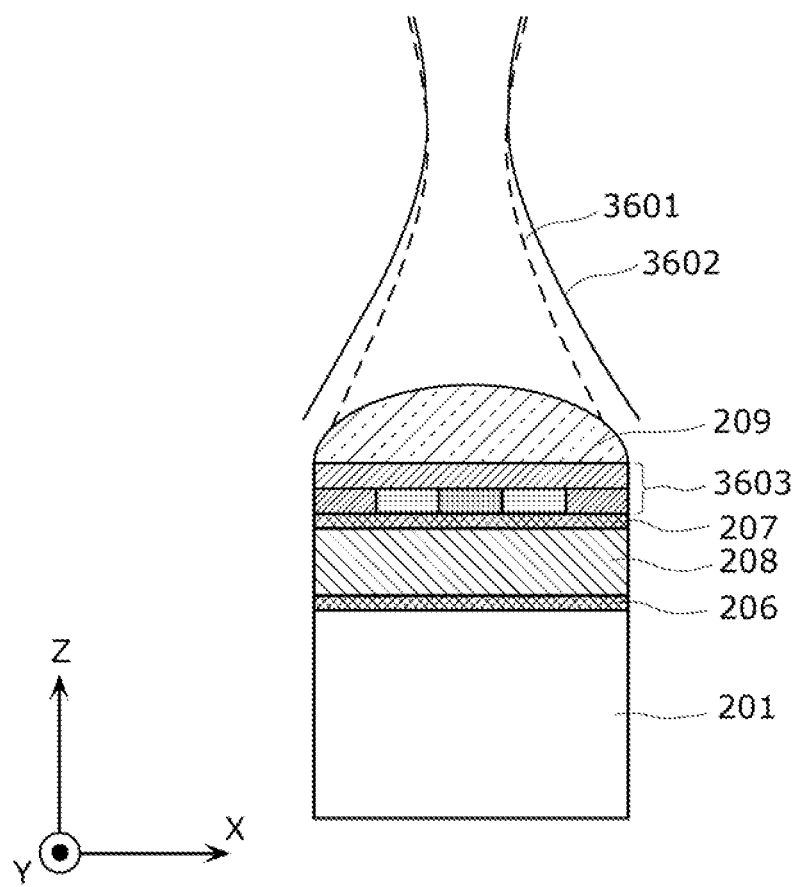
FIG. 36 is a schematic view showing an ultrasonic probe and propagation of ultrasound according to Embodiment 6 of the present invention.

Thus, as shown in FIG. 36, it is preferable that the ultrasonic transducer be designed to include a matching layer 3603 (which includes at least one multi-density layer) according to the present invention so that average frequency of the ultrasound emitted from each of the ends in the X-direction (longitudinal direction of the ultrasonic transducer) is lower than the average frequency of the ultrasound emitted from the central portion. For example the average transmittance frequency is lower when the density of the multi-density layer is higher in any of the examples described in Embodiments 3 to 5. In these cases, it is possible to realize the above by increasing the density of the multi-density layer towards each of the ends in X-direction.

By adopting the structure in which ultrasound having a higher frequency is emitted from the vicinity of the center as indicated by a dotted line 3601, and, the ultrasound having a lower frequency is emitted from a broad region as indicated by a solid line 3602, the thickness of the beam inside the body of the subject can be adjusted approximately the same level even when the ultrasound is focused using one acoustic lens. Reducing the variation in ultrasound pulse waveform according to the location inside the body of the subject makes it possible to reduce degradation of picture quality of the ultrasonic diagnostic image.

Figure 37:
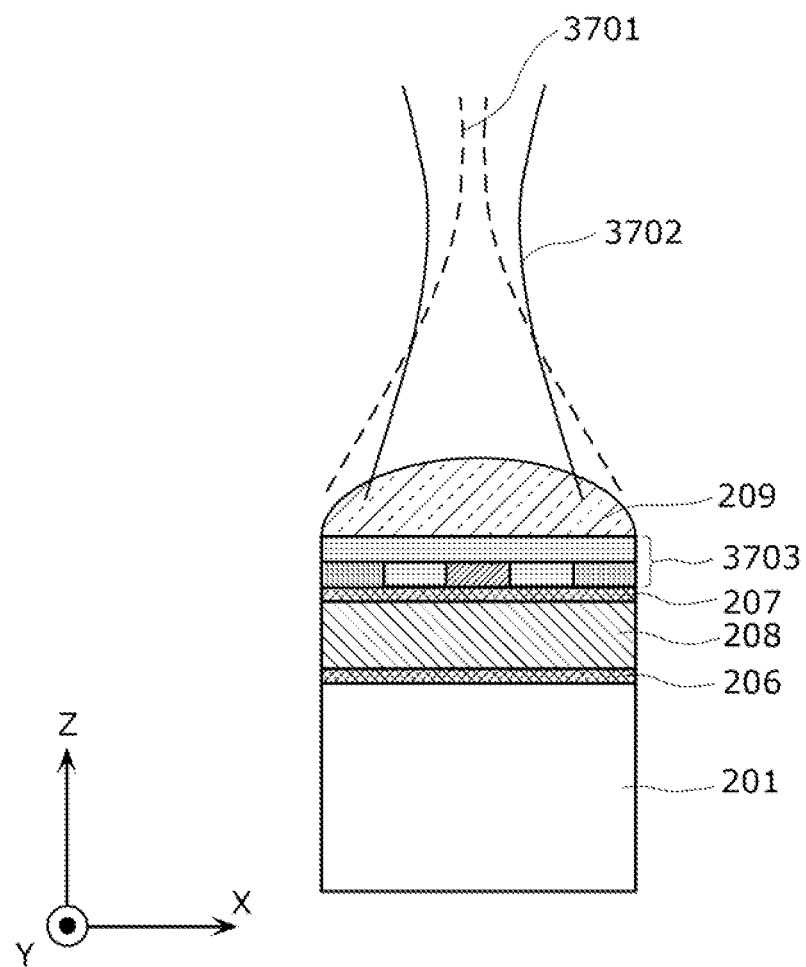
FIG. 37 is a schematic view showing another ultrasonic probe and propagation of ultrasound according to Embodiment 6 of the present invention.

Furthermore, as shown in FIG. 37, designing the ultrasonic transducer to include a matching layer 3703 (which includes at least one multi-density layer) according to the present invention so that the average frequency of the ultrasound emitted from each of the ends in X-direction (longitudinal direction of the ultrasonic transducer) is higher than the average frequency of the ultrasound emitted from the central portion makes it possible to provide the structure which narrows down the ultrasound having a high frequency as indicated by a dotted line 3701, and propagates the ultrasound having low frequency broadly as indicated by a solid line 3702.

Using the structure shown in FIG. 37, separating the ultrasound signal reflected off the subject for each of the frequency and producing an ultrasonic diagnostic image makes it possible to obtain both information which are the ultrasonic diagnostic image obtained from a narrow beam and the ultrasonic diagnostic image obtained from a broad beam.

The ultrasonic diagnostic image obtained from the broad beam is an image created by averaging the data on reflection and scatter in the area. It is possible to perform a position adjustment at high speed by using such image. The ultrasound image obtained from the narrow beam can be created in high contrast without averaging the data on reflection and scatter obtained from the localized area.

The structure shown in FIG. 36 is preferable to realize more generally the ultrasonic diagnosis with a high S/N at a low cost. However, the structure shown in FIG. 37 is preferable for the application, such as detection of an early carcinoma, which requires more detailed image to make a diagnosis.

Furthermore, it is preferable that the ultrasonic probe in which the ultrasonic transducers are arranged to form a one-dimensional array as shown in FIG. 2 include both the ultrasonic transducer having the structure shown in FIG. 36 and the ultrasonic transducer having the structure shown in FIG. 37. This is because it is possible to attain characteristics of both of the transducers by causing each of the ultrasonic transducers to perform ultrasonic vibration at different times.

Furthermore, it is more preferable that the ultrasonic transducers arranged in different orders be arranged to form a one-dimensional array. When each of the ultrasonic transducers transmits ultrasound having a different frequency characteristics, it is possible to transmit ultrasound having wide frequency band.

Furthermore, it is more preferable that the ultrasonic transducers having the same structure be arranged cyclically at constant intervals. For example, the ultrasonic probe in which the ultrasonic transducer having the structure shown in FIG. 36 and the ultrasonic transducer having the structure shown in FIG. 37 are arranged alternately is preferable. Furthermore, for example, the structure in which three ultrasonic transducers, which are two ultrasonic transducers having the structure shown in FIG. 36 and one ultrasonic transducer having the structure shown in FIG. 37, are cyclically arranged as a set of ultrasonic transducers is preferable.

The cyclic arrangement described above makes it possible to attain characteristics of both of the ultrasonic transducers, and thus it is possible to obtain a higher resolution.

It should be noted that although this embodiment described the one-dimensional array type ultrasonic probe, it is apparent that similar advantageous effects are produced with a two-dimensional array type ultrasonic probe.

Furthermore, although the ultrasonic diagnostic device in which the diagnostic device and the ultrasonic probe are connected through a cable has been described, a signal may be transmitted between the diagnostic device and the ultrasonic probe wirelessly.

Although the ultrasonic probe and the ultrasonic diagnostic device according to the present invention have been described thus far, each of the configurations described in DESCRIPTION is merely an example, and it is apparent that various modification can be made without departing from the essence of the present invention.

As described above, the ultrasonic probe according to an aspect of the present invention makes it possible to obtain a high-resolution ultrasonic diagnostic image.

Furthermore, the ultrasonic diagnostic image having a high S/N can be obtained.

Furthermore, the ultrasonic diagnostic image in high resolution with high SAN can be obtained.

Methods for implementing the present invention have been described based on the embodiments. However, the present invention is not limited to these embodiments. Various modifications of the exemplary embodiment as well as embodiments resulting from arbitrary combinations of constituent elements of different exemplary embodiments that may be conceived by those skilled in the art are intended to be included within the scope of the present invention as long as these do not depart from the essence of the present invention.

INDUSTRIAL APPLICABILITY

An ultrasonic probe according to the present invention makes it possible to reduce a side lobe, and arbitrarily design sound field distribution for each frequencies, and thus is useful, for example, as a high-resolution ultrasonic probe for an ultrasonic diagnostic device.

REFERENCE SIGNS LIST 101, 203, 301, 601, 703, 804, 904, 1301, 1401, 1501, 1606, 1607, 2006, 2007, 2008 Matching layer
101a, 101b, 101c, 601a, 602b, 602c, 703a, 703b, 703c, 804a, 804b, 804c, 904a, 904b, 904c, 1601, 1602, 1603, 1604, 1605, 2001, 2002, 2003, 2004, 2005 Matching region
102, 304, 403, 602 Ultrasonic probe
103 Main lobe
104 Side lobe
201 Backing
202 Grounding line
204 Signal line
205 Ultrasonic transducer
206 Signal electrode
207 Ground electrode
208 Piezoelectric body
209 Acoustic lens
302 Main lobe
303 Side lobe
401 Ultrasonic diagnostic device
402 Subject
404 Diagnostic device main body
405 Cable
701, 801, 802, 803, 901, 902, 903 Second matching material
702 First matching material
1502 Third matching material

The invention claimed is:

1. An ultrasonic probe used for ultrasonic diagnosis of a subject, the ultrasonic probe comprising
an ultrasonic transducer including:
a piezoelectric body which generates ultrasound; and
a first matching layer which is disposed in a predetermined direction as seen from the piezoelectric body and is for performing acoustic matching between the piezoelectric body and the subject,
wherein the first matching layer includes a plurality of matching regions which have a uniform thickness in the predetermined direction, are arranged in a direction perpendicular to the predetermined direction, and include at least two matching regions having frequency characteristics of ultrasound transmittance that are different from each other,
wherein the first matching layer includes a plurality of matching materials which have different acoustic impedances, and at least one of the matching materials has tapered shapes parallel to the predetermined direction, and
wherein the number of the tapered shapes in a unit area in one of the matching regions is different from the number of the tapered shapes in a unit area in another one of the matching regions, the unit areas each being in a plane perpendicular to the predetermined direction.

2. The ultrasonic probe according to claim 1, wherein the matching regions include at least two matching regions having densities different from each other.

3. The ultrasonic probe according to claim 1,
wherein each of the tapered shapes has a thickness which continuously increases or decreases in the predetermined direction.

4. The ultrasonic probe according to claim 3, wherein a size of the at least one of the matching materials which has the tapered shapes in one of the matching regions is different from a size of the tapered shapes in another one of the matching regions.

5. The ultrasonic probe according to claim 3, wherein a width of the at least one of the matching materials which has the tapered shapes in one of the matching regions is different from a width of the at least one of the matching materials which has the tapered shapes in another one of the matching regions, the widths each being in a direction in which the matching regions are arranged.

6. The ultrasonic probe according to claim 1, wherein, out of a front surface and a back surface of the first matching layer, a surface which is more distant from the piezoelectric body is flat.

7. The ultrasonic probe according to claim 1, wherein the first matching layer includes a plurality of matching sub-layers stacked in the predetermined direction, and
at least one of the matching sub-layers includes a plurality of matching regions which are arranged in a direction perpendicular to the predetermined direction, and have different frequency characteristics of ultrasound transmittance.

8. The ultrasonic probe according to claim 7, wherein each of the matching sub-layers has a uniform thickness in the predetermined direction.

9. The ultrasonic probe according to claim 1,
wherein the first matching layer is formed from a mixture of a plurality of materials, and
a mixing ratio of the plurality of materials in one of the matching regions is different from a mixing ratio of the plurality of materials in another one of the matching regions.

10. The ultrasonic probe according to claim 1, wherein the first matching layer includes a sintered material.

11. The ultrasonic probe according to claim 1, wherein the first matching layer includes at least silicon dioxide and at least one material out of silver, copper, and an acrylic material.

12. The ultrasonic probe according to claim 1, wherein the first matching layer includes, as material, a plurality of particles, and
among the plurality of particles, particles in one of the matching regions are different in diameter from particles in another one of the matching regions by at least five times.

13. The ultrasonic probe according to claim 1, wherein a width of each of the matching regions in a direction in which the matching regions are arranged is greater than or equal to a wavelength of ultrasound used for the ultrasonic diagnosis.

14. The ultrasonic probe according to claim 2, wherein the first matching layer includes metal nano particles each of which has a diameter less than or equal to one micron, and at least part of the first matching layer is metal bulked, the first matching layer having density determined by a mixing ratio of the metal nano particles to the first matching layer.

15. The ultrasonic probe according to claim 1, wherein the ultrasonic transducer further includes:
- a backing material which is disposed on a side opposite to a side on which the first matching layer is disposed with respect to the piezoelectric body and absorbs ultrasound; and
- a second matching layer disposed between the backing material and the piezoelectric body, and including a plurality of matching regions which are arranged in a direction perpendicular to the predetermined direction and each of which allows ultrasound of different frequency to be transmitted.

16. The ultrasonic probe according to claim 1, wherein the ultrasonic transducer further includes:
- a backing material which is disposed on a side opposite to a side on which the first matching layer is disposed with respect to the piezoelectric body and absorbs ultrasound; and
- a high reflective layer disposed between the backing material and the piezoelectric body, and having a property of reflecting ultrasound.

17. The ultrasonic probe according to claim 1, wherein the ultrasonic transducers are arranged in a one-dimensional array, and
in each of the ultrasonic transducers, an average frequency that is an average value of frequency of ultrasound transmitted through the matching regions located at each of ends of the ultrasonic transducer in a direction in which the matching regions are arranged is lower than an average frequency that is an average value of frequency of ultrasound transmitted through one or more of the matching regions located in the center of the ultrasonic transducer in the direction in which the matching regions are arranged.

18. The ultrasonic probe according to claim 1, wherein the ultrasonic transducers are arranged in a one-dimensional array, and
in each of the ultrasonic transducers, an average frequency that is an average value of frequency of ultrasound transmitted through the matching regions located at each of ends of the ultrasonic transducer in a direction in which the matching regions are arranged is higher than an average frequency that is an average value of frequency of ultrasound transmitted through one or more of the matching regions located in the center of the ultrasonic transducer in the direction in which the matching regions are arranged.

19. The ultrasonic probe according to claim 1, wherein the ultrasonic transducers are arranged in a one-dimensional array, and
the matching regions in one of the ultrasonic transducers are arranged in an order different from an order of the matching regions in another one of the ultrasonic transducers.

20. The ultrasonic probe according to claim 1, wherein the ultrasonic transducers are arranged in a one-dimensional array, and
the matching regions in each of the ultrasonic transducers are arranged in an order to form, in the ultrasonic probe, a cyclic pattern in a direction in which the ultrasonic transducers are arranged.

21. An ultrasonic diagnostic device comprising:
the ultrasonic probe according to claim 1; and
a diagnostic device which generates a signal for causing the piezoelectric body to generate ultrasound, and generates an ultrasonic diagnostic image based on a signal received by the ultrasonic probe from the subject.

* * * * *